US012586663B2

(12) United States Patent
Haas et al.

(10) Patent No.: US 12,586,663 B2
(45) Date of Patent: *Mar. 24, 2026

(54) COPY NUMBER VARIANT CALLER

(71) Applicant: Myriad Women's Health, Inc., South San Francisco, CA (US)

(72) Inventors: Kevin R. Haas, Berkeley, CA (US); Xin Wang, San Francisco, CA (US); Peter V. Grauman, San Francisco, CA (US)

(73) Assignee: Myriad Women's Health, Inc., South San Francisco, CA (US)

( * ) Notice: Subject to any disclaimer, the term of this patent is extended or adjusted under 35 U.S.C. 154(b) by 1132 days.

This patent is subject to a terminal disclaimer.

(21) Appl. No.: 17/554,721

(22) Filed: Dec. 17, 2021

(65) Prior Publication Data

US 2022/0108767 A1 Apr. 7, 2022

Related U.S. Application Data

(63) Continuation of application No. 15/934,839, filed on Mar. 23, 2018, now Pat. No. 11,232,850.

(60) Provisional application No. 62/476,361, filed on Mar. 24, 2017.

(51) Int. Cl.

| | |
|---|---|
| ***G16B 40/00*** | (2019.01) |
| ***G06F 18/20*** | (2023.01) |
| ***G06F 18/2415*** | (2023.01) |
| ***G16B 20/10*** | (2019.01) |
| ***G16B 30/00*** | (2019.01) |
| ***G16B 30/10*** | (2019.01) |
| ***G16B 40/30*** | (2019.01) |
| ***G16B 50/00*** | (2019.01) |
| ***G16H 50/20*** | (2018.01) |

(52) U.S. Cl.

CPC ......... *G16B 40/00* (2019.02); *G06F 18/2415* (2023.01); *G06F 18/295* (2023.01); *G16B 20/10* (2019.02); *G16B 30/00* (2019.02); *G16B 30/10* (2019.02); *G16B 40/30* (2019.02); *G16B 50/00* (2019.02); *G16H 50/20* (2018.01); *G06F 2218/08* (2023.01); *G06F 2218/16* (2023.01); *G06V 2201/04* (2022.01)

(58) Field of Classification Search

CPC ........ G16B 20/00; G16B 20/20; G16B 20/10; G16B 40/00; G16B 40/20; G16B 15/00; G16B 20/40; G16B 30/00; G16B 30/10; G16B 40/30; G16B 5/00; G16B 30/20; G16B 5/20; G16B 50/00; G16B 50/20; G16B 50/30; G16B 50/10; C12Q 2537/16; C12Q 2537/165; G16H 50/20; G16H 10/40; G16H 50/70; G16H 10/60; G16H 15/00; G16H 50/30; G06N 7/005; G06N 20/00; G06N 20/10; G06N 3/0427; G06N 3/08; G06N 5/022; G06N 5/046; G06K 9/6297; G06K 9/00523; G06K 9/0055; G06K 9/6277; G06K 9/62; G06F 17/11

See application file for complete search history.

(56) References Cited

U.S. PATENT DOCUMENTS

| | | | | |
|---|---|---|---|---|
| 5,476,930 | A | 12/1995 | Letsinger et al. | |
| 5,780,613 | A | 7/1998 | Letsinger et al. | |
| 6,258,540 | B1 | 7/2001 | Lo | |
| 7,332,277 | B2 | 2/2008 | Dhallan | |
| 7,799,531 | B2 | 9/2010 | Mitchell et al. | |
| 8,383,338 | B2 | 2/2013 | Kitzman et al. | |
| 9,092,401 | B2 | 7/2015 | Richards et al. | |
| 9,309,556 | B2 | 4/2016 | Myllykangas et al. | |
| 11,232,850 | B2 * | 1/2022 | Haas | G16B 40/00 |
| 2005/0164241 | A1 | 7/2005 | Hahn et al. | |
| 2007/0134658 | A1 | 6/2007 | Bohmer | |
| 2009/0098547 | A1 | 4/2009 | Ghosh | |
| 2011/0257896 | A1 | 10/2011 | Dowds et al. | |
| 2012/0295819 | A1 | 11/2012 | Leamon et al. | |
| 2013/0171185 | A1 | 7/2013 | Settembre et al. | |
| 2013/0316915 | A1 | 11/2013 | Halpern et al. | |
| 2013/0337447 | A1 | 12/2013 | Porreca et al. | |
| 2014/0024536 | A1 | 1/2014 | Richards et al. | |
| 2014/0024541 | A1 | 1/2014 | Richards et al. | |

(Continued)

FOREIGN PATENT DOCUMENTS

| | | | |
|---|---|---|---|
| WO | WO-2010/151842 | A2 | 12/2010 |
| WO | WO-2011/057094 | A1 | 5/2011 |

(Continued)

OTHER PUBLICATIONS

Ahn et al., "Asymmetrical barcode adapter-assisted recovery of duplicate reads and error correction strategy to detect rare mutations in circulating tumor DNA", Scientific Reports, 2017, vol. 7, No. 46678, pp. 1-9.
Amarasinghe et al., "CONVEX: copy number variation estimation in exome sequencing data using HMM", BMC Bioinformatics, 2013, vol. 14, No. Suppl 2, p. S2.
Backenroth et al., CANOES: detecting rare copy number variants from whole exome sequencing data, Nucleic Acids Research, 2014, vol. 42, No. 12, p. e97.
Brynildsrud et al., "CNOGpro: detection and quantification of CNVs in prokaryotic whole genome sequencing data", Bioinformatics, 2015, vol. 31, No. 11, pp. 1708-1715.

(Continued)

*Primary Examiner* — Mary K Zeman
(74) *Attorney, Agent, or Firm* — Foley & Lardner LLP

(57) ABSTRACT

Direct targeted sequencing (DTS) methods and a hidden Markov model (HMV) can be used to call the copy number of a segment of interest within a region of interest. Described herein are methods for calling a copy number variant or a copy number variant abnormality using an HMM, and methods for determining a copy number based on a copy number likelihood model, in a test sequencing library that has be sequenced using DTS methods. Also described herein are methods for determining a copy number of a segment, including accounting for spurious capture probes that may arise from the DTS methods.

13 Claims, 8 Drawing Sheets

(56) References Cited

U.S. PATENT DOCUMENTS

| | | | |
|---|---|---|---|
| 2014/0141982 A1 | 5/2014 | Jacobson et al. | |
| 2014/0162278 A1 | 6/2014 | Richards et al. | |
| 2014/0180594 A1 | 6/2014 | Kim et al. | |
| 2014/0229117 A1 | 8/2014 | Halpern et al. | |
| 2014/0274740 A1 | 9/2014 | Srinivasan et al. | |
| 2015/0044687 A1 | 2/2015 | Schmitt et al. | |
| 2015/0205914 A1 | 7/2015 | Richards et al. | |
| 2015/0275289 A1 | 10/2015 | Otwinowski et al. | |
| 2015/0284712 A1 | 10/2015 | Kurihara et al. | |
| 2016/0115544 A1 | 4/2016 | Elzinga | |
| 2017/0321270 A1 | 11/2017 | Haque et al. | |
| 2017/0355984 A1 | 12/2017 | Evans et al. | |
| 2018/0089364 A1 | 3/2018 | Muzzey et al. | |
| 2018/0201994 A1 | 7/2018 | Beauchamp et al. | |
| 2018/0216103 A1 | 8/2018 | Lai et al. | |
| 2018/0216176 A1 | 8/2018 | Chu et al. | |
| 2022/0108767 A1* | 4/2022 | Haas | G16B 20/10 |

FOREIGN PATENT DOCUMENTS

| | | |
|---|---|---|
| WO | WO-2012/003374 A2 | 1/2012 |
| WO | WO-2012/040387 A1 | 3/2012 |
| WO | WO-2012/078792 A2 | 6/2012 |
| WO | WO-2012/088456 A2 | 6/2012 |
| WO | WO-2013/112923 A1 | 8/2013 |
| WO | WO-2014/138153 A1 | 9/2014 |
| WO | WO-2016/010856 A1 | 1/2016 |
| WO | WO-2016/130704 A2 | 8/2016 |
| WO | WO-2018/144216 A1 | 8/2018 |
| WO | WO-2018/144217 A1 | 8/2018 |

OTHER PUBLICATIONS

Colella et al., "Quanti-SN P: an objective Bayes Hidden Markov Model to detect and accurately map copy number variation using SNP genotyping data", Nucleic Acids Research, 2007, vol. 35, No. 6, pp. 2013-2025.

Crisan et al., "Mutation Discovery in Regions of Segmental Cancer Genome Amplifications with CoNAn-SNV: A Mixture Model for Next Generation Sequencing of Tumors", PLOS One, Aug. 2012, vol. 7, No. 8, p. e41551.

Fromer et al., "Discovery and Statistical Genotyping of Copy-Number Variation from Whole-Exome Sequencing Depth", American Journal of Human Genetics, Oct. 5, 2012, vol. 91, No. 4, pp. 597-607.

Fromer et al., "Using XHMM software to detect copy number variation in whole-exome sequencing data", Current Protocols in Human Genetics, 2014, vol. 81, No. 7, p. 23.1-7.23.21.

Hopmans et al., "A programmable method for massively parallel targeted sequencing", Nucleic Acids Res., 2014, vol. 42, No. 10:e88, pp. 1-16.

International Search Report and Written Opinion issued in corresponding International Application No. PCT/US2018/024062, dated Jul. 11, 2018 (12 pages).

Kang et al., "Design and validation of a next generation sequencing assay for hereditary BRCA1 and BRCA2 mutation testing", Peer J., Jun. 2016, No. 4:e2162, pp. 1-14.

Love, "Statistical analysis of high-throughput sequencing count data", Dissertation, University of Berlin, Jun. 2013, 114 pages.

Mertes et al., "Targeted enrichment of genomic DNA regions for next-generation sequencing", Briefings in Functional Genomics, 2011, vol. 10, No. 6, pp. 374-386.

Miyatake et al., "Detecting copy-number variations in whole-exome sequencing data using the eXome Hidden Markov Model: an "exome-first" approach", Journal of Human Genetics, Jan. 2015, vol. 60, pp. 175-182.

Myllykangas et al. "Efficient targeted resequencing of human germline and cancer genomes by oligonucleotide-selective sequencing", Nat Biotechnol., 2011, vol. 29, No. 11, pp. 1024-1027.

Ng et al., "Targeted capture and massively parallel sequencing of twelve human exomes", Nature, 2009, vol. 461, No. 7261, pp. 272-276.

Poultney et al., "Identification of Small Exonic CNV from Whole-Exome Sequence Data and Application to Autism Spectrum Disorder", American Journal of Human Genetics, Oct. 3, 2013, vol. 93, No. 4, pp. 607-619.

Seiser et al., "Hidden Markov Model-based CNV Detection Algorithms for Illumina Genotyping Microarrays", Cancer Informatics, 2014, vol. 13, p. S7.

Titsias et al., "Statistical Inference in Hidden Markov Models Using κ-Segment Constraints", Journal of the American Statistical Association, Mar. 2016, vol. 111, No. 513, pp. 200-215.

Vysotskaia et al., "Development and validation of a 36-gene sequencing assay for hereditary cancer risk assessment", Peer J., 2017, vol. 5, No. e3046, pp. 1-23.

Zhong et al., "High-throughput Illumina strand-specific RNA sequencing library preparation", Cold Spring Harbor Protocols, 2011, vol. 8, pp. 940-949.

* cited by examiner

FIG. 3A
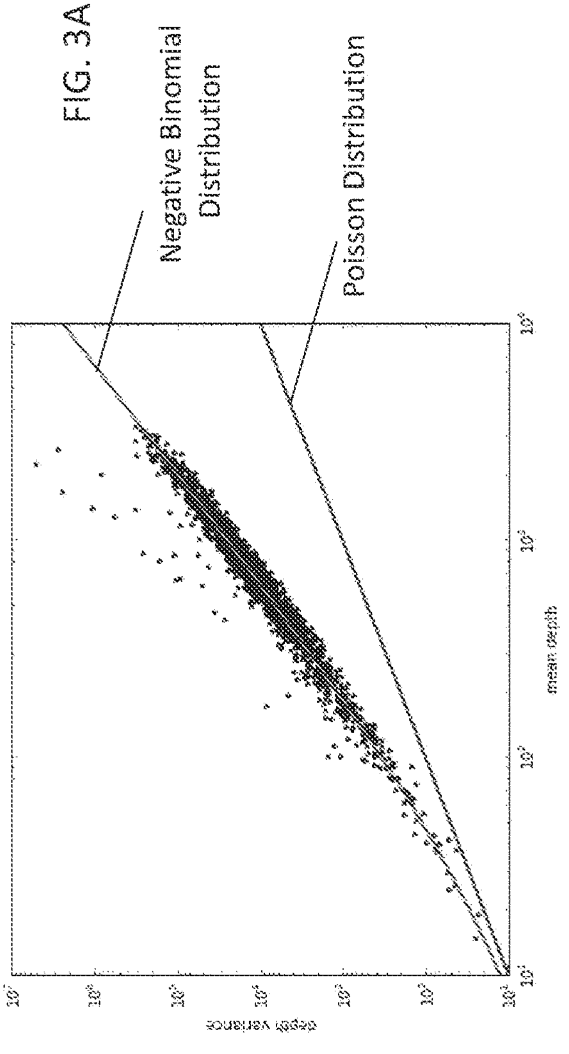
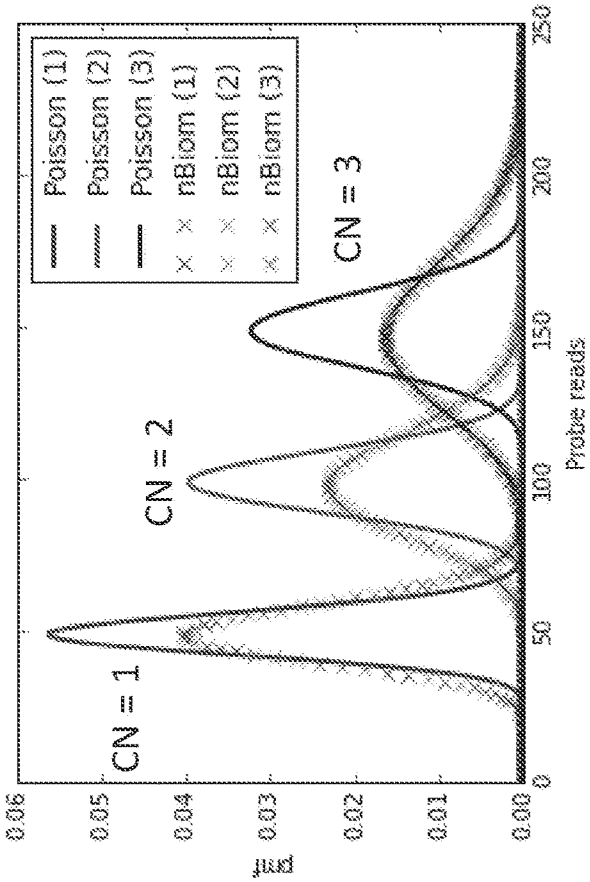
FIG. 3B

COPY NUMBER VARIANT CALLER

CROSS-REFERENCE TO RELATED APPLICATION

This application is a continuation of U.S. application Ser. No. 15/934,839, filed Mar. 23, 2018, which claims priority benefit of U.S. Provisional Application No. 62/476,361, filed on Mar. 24, 2017, entitled "COPY NUMBER VARIANT CALLER," the entire contents of which is incorporated herein by reference for all purposes.

TECHNICAL FIELD

The present invention relates to methods for determining a copy number of a genetic region of interest.

BACKGROUND

There have been many important advances in the understanding of the hereditary susceptibility to cancer and other diseases. Identification of mutations associated with hereditary cancer syndromes and other diseases can lead to reduction in morbidity and mortality through targeted risk management options. The traditional approach for germline testing has been to test for a mutation in a single gene or a limited panel of genes using Sanger sequencing. With advances in next-generation sequencing technology and bioinformatics analysis, testing of multiple genes simultaneously (panel-based testing) at a cost comparable to traditional testing is possible. Panel based testing can provide better accuracy compared to traditional methods as well as improved diagnostic yield with analytical concordance between results from next generation sequencing ("NGS") and the traditional Sanger method for detection of small mutations, such as single nucleotide variants, small deletions, and small insertions.

Despite advancements in NGS technologies in the past years, NGS panels possess analytical limitations which arise from sample preparation, sequencing, mapping, GC content of the targets, target size, and sequence complexity. These factors affect the relationship between read depth and copy number, which is key to copy number variant calls, and as a result the accuracy of the use of NGS techniques for use detecting copy number variants. Such limitations make it challenging for NGS technologies to be used for detection of copy number variants (CNV), such as exon-level copy number variations, larger insertion variants or deletion variants, or rearrangements. Scientific research has suggested that many cancers and complex diseases, such as schizophrenia, are related, at least in part, to copy number variants. Thus, higher accuracy, and accounting for the effect on noise in relating sequencing depth to copy number is especially desirable. To address this concern, some laboratories complement NGS with microarrays, which introduce their own level of complexity and bias to the call. Copy number variants provide valuable information needed for better understanding and characterization of the hereditary susceptibility to cancer and other disease. As such, a method of detecting CNVs with high accuracy is desirable.

The disclosures of all publications, patents, and patent applications referred to herein are each hereby incorporated by reference in their entireties. To the extent that any reference incorporated by reference conflicts with the instant disclosure, the instant disclosure shall control.

SUMMARY

The methods described herein are useful for determining a copy number of an interrogated segment within a region of interest or determining a copy number variant abnormality within a region of interest. A test sequencing library can be enriched using direct targeted sequencing methods, and the enriched sequencing library can be sequenced to determine a number of copies at a segment within a region of interest. The methods can include using a copy number likelihood model and/or a hidden Markov model to accurately determine copy number variants. The methods can include accounting for GC bias, sample noise and/or spurious capture probes.

In some embodiments, there is provided a method for determining a copy number of an interrogated segment within a region of interest comprising: (a) mapping a plurality of sequencing reads generated from a test sequencing library to the interrogated segment, wherein the test sequencing library is enriched using one or more direct targeted sequencing capture probes; (b) determining a number of sequencing reads mapped to the interrogated segment; (c) determining a copy number likelihood model based on an expected number of sequencing reads mapped to the interrogated segment; (d) building a hidden Markov model comprising: (i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model; (e) parameterizing the hidden Markov model by adjusting the copy number likelihood model to fit the determined number of sequencing reads mapped to the interrogated segment; and (f) determining a most probable copy number of the interrogated segment based on the parameterized hidden Markov model.

In some embodiments, there is provided a method for determining a copy number of an interrogated segment within a region of interest comprising: (a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent direct targeted sequencing capture probes; (b) determining a number of sequencing reads mapped to each spatially adjacent segment; (c) determining a copy number likelihood model for each spatially adjacent segment based on an expected number of mapped sequencing reads at the spatially adjacent segment; (d) building a hidden Markov model comprising: (i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; (e) parameterizing the hidden Markov model comprising adjusting each copy number likelihood model to fit the determined number of sequencing reads mapped to each spatially adjacent segment; and (f) determining a most probable copy number of the interrogated segment based on the parameterized hidden Markov model.

In some embodiments, the method further comprises determining a most probable copy number of a section within the region of interest, wherein the section comprises a plurality of spatially adjacent segments comprising the interrogated segment.

In some embodiments, the copy number likelihood model comprises a distribution for two or more copy number states.

In some embodiments, the copy number likelihood model comprises a negative binomial distribution, wherein the negative binomial distribution is not a Poisson distribution.

In some embodiments, the expected number of sequencing reads is based on an average number of mapped sequencing reads at a corresponding segment across a plurality of sequencing libraries and an average number of mapped sequencing reads across a plurality of segments of interest within the test sequencing library, wherein the average number of mapped sequencing reads at a corresponding segment across a plurality of sequencing libraries or the average number of mapped sequencing reads across a plurality of segments of interest within the test sequencing library is a normalized average.

In some embodiments, the copy number likelihood model is adjusted to account for the presence of GC content bias. In some embodiments, the adjustment depends on the GC content of the capture probe corresponding to the interrogated segment or the GC content of the interrogated segment.

In some embodiments, the hidden Markov model comprises a transition probability of the copy number of the interrogated segment for a given copy number of a spatially adjacent segment.

In some embodiments, the hidden Markov model comprises a plurality of transition probabilities of the copy number of a sub-segment in the plurality of sub-segments within the interrogated segment for a given copy number of a spatially adjacent sub-segment. In some embodiments, the transition probability accounts for an average length of a copy number variant. In some embodiments, the transition probability accounts for a prior probability of a copy number variant at the interrogated segment or a spatially adjacent segment. In some embodiments, the average length of a copy number variant or the probability of a copy number variant at the interrogated segment are determined based on observations in a human population.

In some embodiments, parameterizing the hidden Markov model comprises accounting for one or more spurious capture probes. In some embodiments, accounting for one or more spurious capture probes comprises weighting the one or more observation states in the plurality of observation states with a spurious capture probe indicator. In some embodiments, the spurious capture probe indicator is determined using a Bernoulli process. In some embodiments, accounting for one or more of the capture probes being spurious comprises using expectation-maximization. In some embodiments, if a capture probe is determined to be spurious, the likelihood information from that capture probe is disregarded in the copy number likelihood model.

In some embodiments, the parameterizing of the hidden Markov model comprises accounting for noise in the number of mapped sequencing reads. In some embodiments, accounting for noise in the number of mapped sequencing reads comprises adjusting the copy number likelihood model. In some embodiments, adjusting the copy number likelihood model to account for the noise comprises an expectation-maximization step. In some embodiments, the expectation-maximization step comprises weighing a level of noise in the number of mapped sequencing reads from the test sequencing library. In some embodiments, the expectation-maximization step comprises using a Quasi-Newtonian solver. In some embodiments, the most probable copy number of the interrogated segment is not called if the noise in the number of mapped sequencing reads is above a predetermined threshold.

In some embodiments, sequencing reads from overlapping capture probes are merged.

In some embodiments, a Viterbi algorithm, a Quasi-Newton solver, or a Markov chain Monte Carlo is used to determine the most probable copy number of the interrogated segment.

In some embodiments, the method further comprises determining a confidence of the most probable copy number of the segment.

In some embodiments, the region of interest is a region within genomic DNA.

In some embodiments, the test sequencing library is derived from cell-free DNA.

In some embodiments, the method comprises reporting the most probable copy number of the interrogated segment. In some embodiments, the method comprises reporting a copy number variant. In some embodiments, the copy number variant is reported to a patient or a healthcare provider. In some embodiments, the method comprises providing a medical diagnosis based on the most probable copy number of the interrogated segment. In some embodiments, the method comprises suggesting a treatment regimen based on the most probable copy number of the interrogated segment.

In some embodiments, there is provided a method for determining a copy number variant abnormality within a region of interest, comprising: (a) mapping a plurality of sequencing reads generated from a test sequencing library to an interrogated segment within the region of interest, wherein the test sequencing library is enriched using one or more direct targeted sequencing capture probes; (b) determining a number of sequencing reads mapped to the interrogated segment; (c) determining a copy number likelihood model based on an expected number of sequencing reads mapped to the interrogated segment; (d) building a hidden Markov model comprising: (i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model; (e) parameterizing the hidden Markov model by adjusting the copy number likelihood model to fit the determined number of sequencing reads mapped to the interrogated segment; and (f) determining a most probable copy number of the interrogated segment based on the parameterized hidden Markov model; (g) determining a copy number variant abnormality based on the most probable copy number of the interrogated segment.

In some embodiments, there is provided a method for determining a copy number variant abnormality within a region of interest, comprising: (a) mapping a plurality of sequencing reads generated from a test sequencing library to a plurality of spatially adjacent segments, wherein the plurality of spatially adjacent segments comprises an interrogated segment, and wherein the test sequencing library is enriched using a plurality of spatially adjacent direct targeted sequencing capture probes; (b) determining a number of sequencing reads mapped to each spatially adjacent segment; (c) determining a copy number likelihood model for each spatially adjacent segment based on an expected number of mapped sequencing reads at the spatially adjacent segment; (d) building a hidden Markov model comprising: (i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; (e) parameterizing the hidden Markov model comprising adjusting each copy number likelihood model to fit the determined number of sequencing reads mapped to each spatially adjacent segment; and (f) determining a most probable copy number of the interrogated segment based on the parameterized hidden Markov model; (g) determining a copy number variant abnormality based on the most probable copy number of the interrogated segment.

In some embodiments, there is provided a method for determining a copy number of an interrogated segment within a region of interest comprising: (a) mapping a plurality of sequencing reads generated from a test sequencing library to a plurality of segments within a region of interest, wherein the test sequencing library is enriched using a plurality of capture probes, and wherein the plurality of segments comprises the interrogated segment; (b) determining a number of sequencing reads mapped to each segment; (c) determining a copy number likelihood model for the segment based on an expected number of mapped sequencing reads at each segment, wherein the expected number of mapped sequencing reads is corrected for GC content of the segment; and (d) determining a most probable copy number of the interrogated segment based on the copy number likelihood model.

In some embodiments, there is provided a method for determining a copy number of an interrogated segment within a region of interest comprising: (a) mapping a plurality of sequencing reads generated from a test sequencing library to the interrogated segment, wherein the test sequencing library is enriched using a plurality of capture probes; (b) determining a number of sequencing reads mapped to the interrogated segment; (c) determining a copy number likelihood model based on an expected number of sequencing reads mapped to the interrogated segment, wherein the expected number of mapped sequencing reads is corrected for GC content of the interrogated segment; (d) building a hidden Markov model comprising: (i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model; (e) parameterizing the hidden Markov model by adjusting the copy number likelihood model to fit the determined number of sequencing reads mapped to the interrogated segment; and (f) determining a most probable copy number of the interrogated segment based on the parameterized hidden Markov model.

In some embodiments, there is provided a method for determining a copy number of an interrogated segment within a region of interest comprising: (a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent capture probes; (b) determining a number of sequencing reads mapped to each spatially adjacent segment; (c) determining a copy number likelihood model for each spatially adjacent segment based on an expected number of mapped sequencing reads at the spatially adjacent segment, wherein the expected number of mapped sequencing reads is corrected for GC content of the spatially adjacent segment; (d) building a hidden Markov model comprising: (i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; (e) parameterizing the hidden Markov model comprising adjusting each copy number likelihood model to fit the determined number of sequencing reads mapped to each spatially adjacent segment; and (f) determining a most probable copy number of the interrogated segment based on the parameterized hidden Markov model.

In some embodiments of the above methods, the capture probes are direct targeted sequencing capture probes. In some embodiments, the capture probes enrich the sequencing library using hybrid capture techniques. In some embodiments, the expected number of sequencing reads is corrected for the GC content by multiplying the expected number of sequencing reads at any given segment by a GC bias correction factor for that segment, wherein the GC bias correction factor is determined for the test sequencing library. In some embodiments, the GC bias correction factor is determined by: fitting a second order function to a plurality of data points, wherein the data points each comprises a normalized number of sequencing reads mapped to a segment and the GC content of that segment, and wherein the plurality of data points represent a plurality of segments enriched by the capture probes in the test sequencing library; and defining the GC bias correction factor to be the normalized number of sequencing reads determined by the second order function for the GC content of the segment.

In some embodiments, there is provided a method for determining a copy number of an interrogated segment within a region of interest comprising: (a) mapping a plurality of sequencing reads generated from a test sequencing library to the interrogated segment, wherein the test sequencing library is enriched using one or more capture probes; (b) determining a number of sequencing reads mapped to the interrogated segment; (c) determining a copy number likelihood model based on an expected number of sequencing reads mapped to the interrogated segment; (d) building a hidden Markov model comprising: (i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model; (e) parameterizing the hidden Markov model by adjusting the copy number likelihood model to fit the determined number of sequencing reads mapped to the interrogated segment and accounting for one or more spurious capture probes; and (f) determining a most probable copy number of the interrogated segment based on the parameterized hidden Markov model.

In some embodiments, there is provided a method for determining a copy number of an interrogated segment within a region of interest comprising: (a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent direct targeted sequencing capture probes; (b) determining a number of sequencing reads mapped to each spatially adjacent segment; (c) determining a copy number likelihood model for each spatially adjacent segment based on an expected number of mapped sequencing reads at the spatially adjacent segment; (d) building a hidden Markov model comprising: (i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; (e) parameterizing the hidden Markov model comprising adjusting each copy number likelihood model to fit the determined number of sequencing reads mapped to each spatially adjacent segment and accounting for one or more spurious capture probes; and (f) determining a most probable copy number of the interrogated segment based on the parameterized hidden Markov model.

In some embodiments, accounting for one or more spurious capture probes comprises weighting the one or more observation states in the plurality of observation states with a spurious capture probe indicator. In some embodiments, the spurious capture probe indicator is determined using a Bernoulli process. In some embodiments, accounting for one or more of the capture probes being spurious comprises using expectation-maximization. In some embodiments, the most probable copy number of the interrogated segment or the one or more sub-segments of the interrogated segment is not called if the capture probe associated with the interrogated segment is determined to be spurious. In some embodiments, the most probable copy number of the interrogated segment or the one or more sub-segments of the interrogated segment is not called if the probability of a capture probe being spurious is above a predetermined threshold. In some embodiments, the capture probes are direct targeted sequencing capture probes. In some embodiments, the capture probes enrich the sequencing library using hybrid capture techniques.

In some embodiments, the interrogated segment is at least 100 bases in length.

Also provided herein is a computer system comprising a computer-readable medium comprising instructions for carrying out any of the methods described herein.

BRIEF DESCRIPTION OF THE DRAWINGS

FIG. 3A shows a plot of the sequencing depth variance against the mean number of sequencing reads ("mean depth") for approximately 2500 capture probes used to enrich a sequencing library for a region of interest for a plurality of different samples. The data was fit using a negative binomial distribution, wherein the negative binomial distribution is not a Poisson distribution. As a comparison, a Poisson distribution is also illustrated, which assumes a linear relationship between dispersion and mean depth. As can be seen in the graph, the variance to depth distribution across the probes follows a negative binomial distribution and not simply a Poisson distribution.

FIG. 3B shows a copy number likelihood model comprising negative binomial distributions, wherein the negative binomial distributions are not Poisson distributions or Poisson distributions for a copy number of 1, 2, or 3 copies of a segment. The distributions are probability mass functions (pmf) as a function of the number of sequencing reads from the capture probe corresponding with the segment. "CN"=Copy Number.

DETAILED DESCRIPTION

Figure 1:
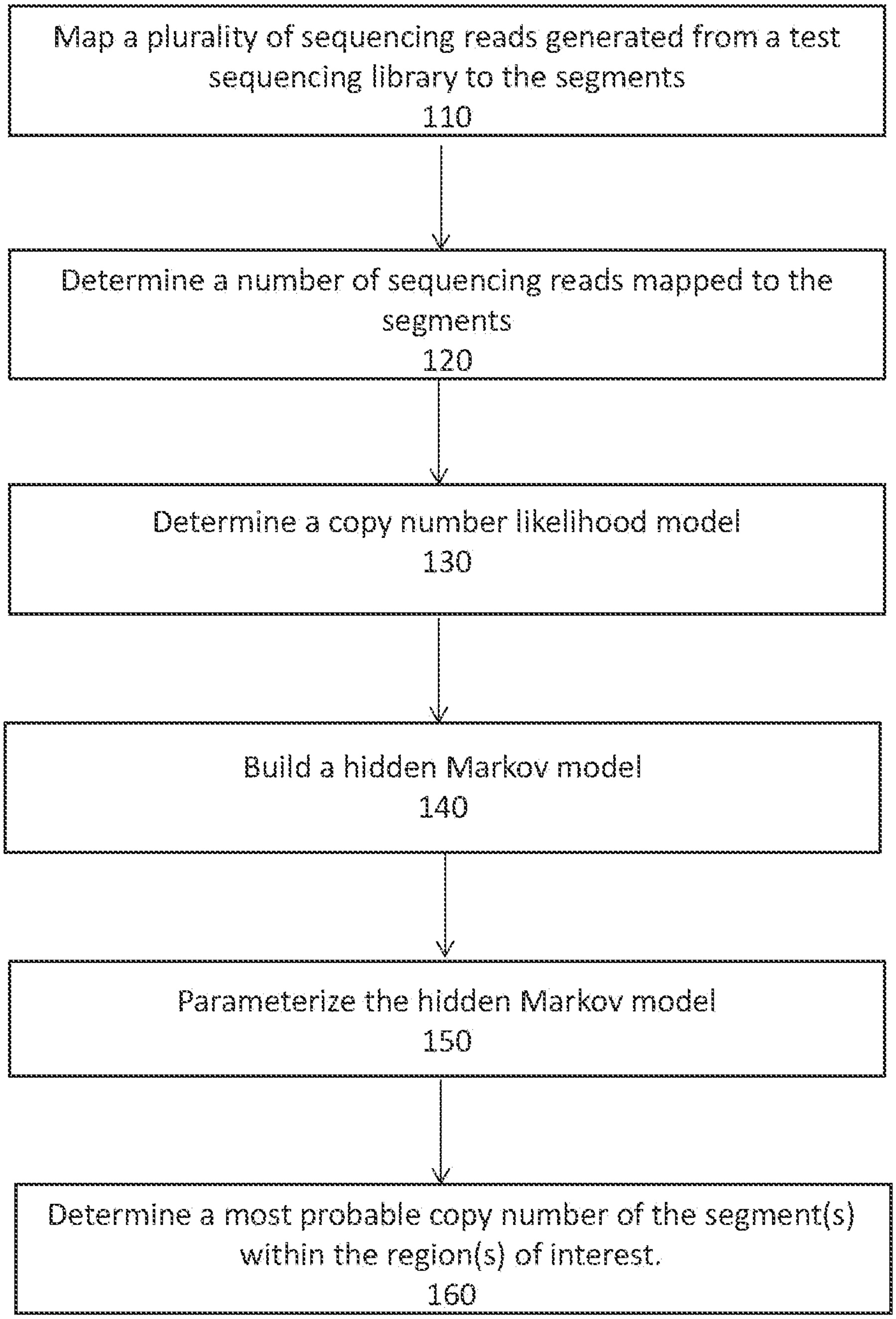
FIG. 1 shows a flow chart of one embodiment of a method for determining a copy number of a segment.

The methods described herein allow for accurate determination of the number of copies of an interrogated segment of a genome, such as a gene or gene segment. Accurate copy number calling allows for better diagnosis of certain genetic anomalies, which aid in making important medical decisions. The methods include the use of a hidden Markov model (HMM) to determine a most probable copy number for an interrogated segment of a test sequencing library that has been enriched using direct targeted sequencing (DTS) methods. DTS methods provide high resolution targeting of interrogated sequences, and the HMM caller described herein is substantially benefitted by the large amount of collected data for copy number calling. To further increase the accuracy of the HMM caller, sequencing depth artifacts that can arise from direct targeted sequencing methods can be accounted for. Such sequencing depth artifacts may include, for example, GC bias correction and determination of spurious probes. Additionally, the methods described herein provide for accurate copy number calling when the sequencing reads are produced from a noisy sequencing library.

In some embodiments, the method for determining a copy number of an interrogated segment within a region of interest comprising (a) mapping a plurality of sequencing reads generated from a test sequencing library to the interrogated segment, wherein the test sequencing library is enriched using one or more direct targeted sequencing capture probes; (b) determining a number of sequencing reads mapped to the interrogated segment; (c) determining a copy number likelihood model based on an expected number of sequencing reads mapped to the interrogated segment; (d) building a hidden Markov model comprising: (i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model; (e) parameterizing the hidden Markov model by adjusting the copy number likelihood model to fit the determined number of sequencing reads mapped to the interrogated segment; and (f) determining a most probable copy number of the interrogated segment based on the parameterized hidden Markov model. In some embodiments, the copy number likelihood model is optimized to account for noise. Noise can arise, for example, from GC content bias of a test sequencing library, from preparation of the test sequencing library, or from hybridization by the capture probes. In some embodiments the copy number likelihood model is a statistical distribution. In some embodiments the copy number likelihood model is a negative binomial distribution (such as a generalized Poisson negative binomial distribution, wherein the negative binomial distribution is not simply a Poisson distribution). In some embodiments the hidden Markov model comprises a transition probability of the copy number of the interrogated segment for a given copy number of a spatially adjacent segment. In some embodiments the hidden Markov model comprises a plurality of transition probabilities of the copy number of a sub-segment in the plurality of sub segments within the interrogated segment for a given copy number of a spatially adjacent sub-segment. In some embodiments a transition probability of the hidden Markov model accounts for an average length of a copy number variant and a probability of a copy number variant at the segment.

Further provided herein is a method for determining a copy number of an interrogated segment within a region of interest comprising: (a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent direct targeted sequencing capture probes; (b) determining a number of sequencing reads mapped to each spatially adjacent segment; (c) determining a copy number likelihood model for each spatially adjacent segment based on an expected number of mapped sequencing reads at the spatially adjacent segment; (d) building a hidden Markov model comprising: (i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; (e) parameterizing the hidden Markov model comprising adjusting each copy number likelihood model to fit the determined number of sequencing reads mapped to each spatially adjacent segment; and (f) determining a most probable copy number of the interrogated segment based on the parameterized hidden Markov model.

Also described herein are methods for determining a copy number variant abnormality within a region of interest, comprising (a) mapping a plurality of sequencing reads generated from a test sequencing library to an interrogated segment within the region of interest, wherein the test sequencing library is enriched using one or more direct targeted sequencing capture probes; (b) determining a number of sequencing reads mapped to the interrogated segment; (c) determining a copy number likelihood model based on an expected number of sequencing reads mapped to the interrogated segment; (d) building a hidden Markov model comprising: (i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model; (e) parameterizing the hidden Markov model by adjusting the copy number likelihood model to fit the determined number of sequencing reads mapped to the interrogated segment; and (f) determining a most probable copy number of the interrogated segment based on the parameterized hidden Markov model; (g) determining a copy number variant abnormality based on the most probable copy number of the interrogated segment.

In addition, there is provided herein a method for determining a copy number variant abnormality within a region of interest, comprising: (a) mapping a plurality of sequencing reads generated from a test sequencing library to a plurality of spatially adjacent segments, wherein the plurality of spatially adjacent segments comprises an interrogated segment, and wherein the test sequencing library is enriched using a plurality of spatially adjacent direct targeted sequencing capture probes; (b) determining a number of sequencing reads mapped to each spatially adjacent segment; (c) determining a copy number likelihood model for each spatially adjacent segment based on an expected number of mapped sequencing reads at the spatially adjacent segment; (d) building a hidden Markov model comprising: (i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; (e) parameterizing the hidden Markov model comprising adjusting each copy number likelihood model to fit the determined number of sequencing reads mapped to each spatially adjacent segment; and (f) determining a most probable copy number of the interrogated segment based on the parameterized hidden Markov model; (g) determining a copy number variant abnormality based on the most probable copy number of the interrogated segment.

In another aspect, there is provided a method for determining a copy number of an interrogated segment within a region of interest comprising: (a) mapping a plurality of sequencing reads generated from a test sequencing library to a plurality of segments within a region of interest, wherein the test sequencing library is enriched using a plurality of capture probes, and wherein the plurality of segments comprises the interrogated segment; (b) determining a number of sequencing reads mapped to each segment; (c) determining a copy number likelihood model for the segment based on an expected number of mapped sequencing reads at each segment, wherein the expected number of mapped sequencing reads is corrected for GC content bias of the segment; and (d) determining a most probable copy number of the interrogated segment based on the copy number likelihood model.

In some embodiments, there is a method for determining a copy number of an interrogated segment within a region of interest comprising: (a) mapping a plurality of sequencing reads generated from a test sequencing library to the interrogated segment, wherein the test sequencing library is enriched using a plurality of capture probes; (b) determining a number of sequencing reads mapped to the interrogated segment; (c) determining a copy number likelihood model based on an expected number of sequencing reads mapped to the interrogated segment, wherein the expected number of mapped sequencing reads is corrected for GC content of the interrogated segment; (d) building a hidden Markov model comprising: (i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model; (e) parameterizing the hidden Markov model by adjusting the copy number likelihood model to fit the determined number of sequencing reads mapped to the interrogated segment; and (f) determining a most probable copy number of the interrogated segment based on the parameterized hidden Markov model.

In some embodiments, there is a method for determining a copy number of an interrogated segment within a region of interest comprising: (a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent capture probes; (b) determining a number of sequencing reads mapped to each spatially adjacent segment; (c) determining a copy number likelihood model for each spatially adjacent segment based on an expected number of mapped sequencing reads at the spatially adjacent segment, wherein the expected number of mapped sequencing reads is corrected for GC content of the spatially adjacent segment; (d) building a hidden Markov model comprising: (i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; (e) parameterizing the hidden Markov model comprising adjusting each copy number likelihood model to fit the determined number of sequencing reads mapped to each spatially adjacent segment; and (f) determining a most probable copy number of the interrogated segment based on the parameterized hidden Markov model.

In some embodiments, there is a method for determining a copy number of an interrogated segment within a region of interest comprising: (a) mapping a plurality of sequencing reads generated from a test sequencing library to the interrogated segment, wherein the test sequencing library is enriched using one or more capture probes; (b) determining a number of sequencing reads mapped to the interrogated segment; (c) determining a copy number likelihood model based on an expected number of sequencing reads mapped to the interrogated segment; (d) building a hidden Markov model comprising: (i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model; (e) parameterizing the hidden Markov model by adjusting the copy number likelihood model to fit the determined number of sequencing reads mapped to the interrogated segment and accounting for one or more spurious capture probes; and (f) determining a most probable copy number of the interrogated segment based on the parameterized hidden Markov model.

In some embodiments, there is a method for determining a copy number of an interrogated segment within a region of interest comprising: (a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent direct targeted sequencing capture probes; (b) determining a number of sequencing reads mapped to each spatially adjacent segment; (c) determining a copy number likelihood model for each spatially adjacent segment based on an expected number of mapped sequencing reads at the spatially adjacent segment; (d) building a hidden Markov model comprising: (i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; (e) parameterizing the hidden Markov model comprising adjusting each copy number likelihood model to fit the determined number of sequencing reads mapped to each spatially adjacent segment and accounting for one or more spurious capture probes; and (f) determining a most probable copy number of the interrogated segment based on the parameterized hidden Markov model.

In some embodiments, the methods described herein further comprise reporting the most probable copy number of the interrogated segment or a sub-segment of the interrogated segment. The methods can also include reporting a copy number variant, which can be reported to a patient or a healthcare provider (such as a doctor or a hospital). In some embodiments, the methods described herein further comprise providing a medical diagnosis based on the most probable copy number of the interrogated segment or a sub-segment of the interrogated segment. In some embodiments, the methods described herein further comprise suggesting a treatment regimen based on the most probable copy number of the interrogated segment or a sub-segment of the interrogated segment.

Sequencing libraries derived from patient samples can be sequenced to obtain a number of sequencing reads. The copy number of a segment is related to the sequencing depth (that is, the number of sequencing reads or a normalized number of sequencing reads) at that segment. The present disclosure describes a method of using the sequencing depth at the segment to determine the presence of a copy number state at the segment. The sequencing depth may be obtained by determining the sequencing reads mapped to that segment. The sequencing depth may be obtained by determining the sequencing reads mapped to a capture probe corresponding to that segment. The method takes into consideration several factors associated with the sequencing technology to optimize the call so that it is more accurate.

Determining the mapped number of sequencing reads for a segment depends at least in part, to the actual copy number state of a segment. The vast majority of genetic regions in mammals are diploid and as such it is expected that, generally, there will be two copies of a genetic segment. This might not always be the case. For example, some regions of the genome are not diploid due to their location (being located on the Y chromosome for example). Other regions of the genome lose their diploidy as a result of functional specialization of some cells, such as immune cells, that result in genomic re-arrangements. However, regardless of these deviations from the norm, the copy number state of most genomic regions is expected to be two, and a deviation from a copy number state of two is expected to be reflected in the number of mapped sequencing reads.

Mapping sequencing reads to a segment can be preceded by one or more upstream steps, such as sample preparation, including fragmentation, formation of the sequencing library (for example, by ligating sequencing adapters to the nucleic acid molecules in the sequencing library), and sequencing the sequencing library. Noise in the sequencing depth at any of these upstream steps can introduce noise to the number of sequencing reads. Furthermore, the various capture probes in a capture probe library may not behave identically. For example, certain segments within the region of interest may not allow for ideal capture probe design, which can lead to spurious capture probes. Thus, using the determined number of mapped sequencing reads to determine the copy number state of a segment is less direct than recognizing the existing dependency between the copy number state of a segment and the determined number of mapped sequencing reads at the segment. The methods of the present invention allow for a copy number call of an interrogated segment within the region of interest to be made using a hidden Markov model, which is parameterized and optimized to account for the dependency between the number of mapped sequencing reads and the copy number state of the segment. The hidden Markov model can also account for various sources and levels of confounders. This method allows for a particularly effective and efficient process for determining copy numbers of interrogated segments or sub-segments within a region of interest, and for determining a copy number variant abnormality within the region of interest.

In some embodiments of the present invention, the sequencing library is enriched for the region of interest using direct targeted sequencing. Direct targeted sequencing uses a capture probe library comprising a plurality of capture probes that hybridize to nucleic acid molecules in the sequencing library. The capture probes are designed to hybridize to segments within the region of interest, and each capture probe has a corresponding segment. The region of interest is therefore determined by the capture probes used to enrich the sequencing library. The capture probes are extended using the nucleic acid molecules hybridized to the capture probe as a template. The extended capture probe can then be sequenced to obtain the sequence a portion (that is, the portion corresponding to the segment from the region of interest) of the nucleic acid molecule. Because the sequence of the capture probe itself is determined, the segment corresponding to the capture probe begins following the terminus of the capture probe. In some embodiments, the extended capture probe is amplified to obtain additional copies. Amplification of the extended capture probe can also introduce artifacts in the sequencing depth, which can be normalized as described herein. U.S. Pat. No. 9,309,556, entitled "Direct Capture, Amplification and Sequencing of Target DNA using Immobilized Primers"; U.S. Pat. No. 9,092,401, entitled "System and Method for Detecting Genetic Variation"; U.S. Patent App. No. 2014/0024541, entitled "Methods and Compositions for High-throughput Screening"; Myllykangas et al. "Efficient targeted resequencing of human germline and cancer genomes by oligonucleotide-selective sequencing." *Nat Biotechnol.* 29(11): 1024-7 (2011); and Hopmans et al., "A programmable method for massively parallel targeted sequencing." *Nucleic Acids Res.* 42(10):e88 (2014) describe embodiments of direct targeted sequencing. Direct targeted sequencing need not be performed using surface-based methods, but can also be performed in solution.

In some embodiments, the sequencing library is enriched for the region of interest using methods other than direct targeted sequencing. For example, the sequencing library can be enriched using hybrid capture techniques, which include combining the sequencing library with a capture probe library to hybridize the capture probes with nucleic acid molecules in the sequencing library. The hybridized nucleic acid molecules can then be isolated from the rest of the sequencing library (for example, by using biotinylated capture probes and using streptavidin beads to separate the hybridized molecules). The nucleic acid molecules in the enriched sequencing library can then be sequenced. Because the nucleic acid molecules from the sequencing library are directly sequenced (as opposed to direct targeted sequencing methods), the capture probes do not necessarily correspond with specific segments within the region of interest. Instead, the sequencing depth at any given base within the region of interest can be determined by the number of sequencing reads at that base.

Provided herein are definitions, explanations, examples and descriptions that allow one skilled in the art to understand the scope of the methods provided, and enable one skilled in the art to practice the invention. It is to be understood that one, some or all of the properties of the various embodiments described herein may be combined to form other embodiments of the present invention. The section headings used herein are for organizational purposes only and are not to be construed as limiting the subject matter described.

Definitions

As used herein, the singular forms "a," "an," and "the" include the plural reference unless the context clearly dictates otherwise.

Reference to "about" or "approximately" a value or parameter herein includes (and describes) variations that are directed to that value or parameter per se. For example, description referring to "about X" includes description of "X."

The term "average" as used herein refers to either a mean or a median, or any value used to approximate the mean or the median, unless the context clearly indicates otherwise.

A "capture probe" refers to a DNA or RNA which hybridize to nucleic acid molecules having segments with complementary sequences (or sufficiently complementary sequences to allow for hybridization under normal hybridization conditions) to the probes. The nucleic acid molecules are present in a sequencing library.

"Copy number likelihood" refers to the likelihood of a copy number state at a segment or sub-segment of interest. The copy number likelihood can be determined by use of a statistical model.

"Copy number likelihood model" refers to a statistical model used to determine a likelihood of one or more copy number states of a segment of interest, given a number of mapped sequencing reads at that segment. The copy number likelihood model includes a statistical distribution for each copy number state covered by the model, and each distribution reflects the probability that the copy number state is correct for a given number of mapped sequencing reads.

"Copy number variant" or "CNV" refers to a deviation in the copy number state from a wild type. A "wild-type" as used herein refers to a predetermined copy number state for a particular segment that is considered normal. The determination of what is "wild-type" can be made based on human, mammal or other animal population data. The determination of what a "wild-type" is can also be made based on reference runs, internal experiments and data generated from such experiments.

A "direct targeted sequencing capture probe" is a capture probe that is used to enrich a sequence from a sequencing library using direct targeted sequencing.

An "interrogated segment" refers to a segment for which it is desirable to determine the copy number state. The interrogated segment is within a region of interest. The interrogated segment can be divided into sub-segments. Such sub-segments may be as small as one base pair, but no longer than the length of the interrogated segment. In the context of the hidden Markov model, the copy number state of the interrogated segment is a hidden state of the model. It is desirable that by solving the hidden Markov model a most probable copy number state for the interrogated segment can be determined.

A "noisy sequencing library" or "noise" from a sequencing library refers to a sequencing library that generates poor data across one or more capture probes. During preparation or sequencing of the sequencing library, several sources of noise exist. For example oligonucleotide collection, storage, or fragmentation can compromise the integrity of the oligonucleotide, which in turn can affect how the oligonucleotide is amplified, sequenced, and mapped. This leads to "noise" which comes from the preparation or inherent characteristics of the sequencing library.

"Optimization" or "optimizing" as used herein refers to finding the best solution for a given objective given predetermined constrains. Adjusting a model comprises optimizing a model. Maximizing is a type of optimizing. A model always comprises a plurality of parameters. Optimizing a model is to find a set of parameters that would maximize the likelihood of correctly estimating an unknown parameter of the model. It is also understood that optimization may include several steps. For example a parameter in the hidden Markov model may undergo several rounds of expectation maximization.

A "segment" refers to a nucleotide chain comprising two or more bases. A segment can be sub-divided into one or more "sub-segments." A "sub-segment" can be as small as one nucleotide but not longer than the segment in which is it is located. A region of interest can be divided into one or more segments. The segments can be, but need not be, contiguous. Therefore a region of interest can optionally include non-contiguous sub-regions. The segments can be of the same length or of different lengths. Two or more segments within a region of interest can be grouped to make a section within the region of interest. The segments that make up a section within the region of interest may be, but need not be contiguous.

A "spurious capture probe" refers to an unreliable capture probe because it generates artifacts in the number of sequencing reads. The artifacts can be due to sub-par sequencing reads, inconsistent sequencing reads, sequencing reads of length that fall below a predetermined level, a number of sequencing reads that fall below a predetermined level, or displays poor quality when compared to other capture probes.

"Spatially adjacent segments" refer to a set of sequential segments that are located within the same chromosome, but need not be contiguous. That is, two spatially adjacent segments can be separated by a number of intervening nucleotides but not by intervening segments outside of the set of spatially adjacent segments. The copy number of any intervening nucleotides if the two spatially adjacent segments are not contiguous may be inferred through the hidden Markov model. "Spatially adjacent capture probes," including "spatially adjacent direct targeted sequencing capture probes," refer to capture probes that correspond to the spatially adjacent segments.

It is understood that aspects and variations of the invention described herein include "consisting" and/or "consisting essentially of" aspects and variations.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

Methods of Determining a Copy Number

The present disclosure provides methods to determine the copy number of an interrogated segment (or sub-segment of the interrogated segment) of a region of interest, or a copy number variant abnormality within a region of interest, based on the determined number of mapped sequencing reads at that segment. The methods include determining a copy number likelihood model based on an expected number of mapped sequencing reads for one or more copy number states. Expectation-Maximization (EM) can be used to enable latent parameter estimation and optimization of the model. Several additional steps and adjustments to the model can be used to account for other factors that affect the relationship between a copy number and the number of mapped sequencing reads. The information is used to parameterize the hidden Markov model which can then be used to determine a most probable copy number state at an interrogated segment. Methods for building the copy number likelihood model, Expectation-Maximization implementation, adjustment to the model to account for multiple factors, parameterization of the hidden Markov model as well as methods of solving the various steps and the model overall, are provided generally below. In one preferred embodiment the efficiency and reliability of the hidden Markov model, relies on the use of Expectation-Maximization (EM) to enable parameter estimation for several latent variables.

In brief, the methods for determining a copy number of a segment or sub-segment include (1) determining the number of sequencing reads mapped to an interrogated segment; (2) building and parameterizing a hidden Markov model by determining a copy number likelihood model; and (3) determining a most probable copy number of the interrogated segment (or a sub-segment of the interrogated segment) using the parameterized hidden Markov model. In some embodiments, the methods provided herein also include steps to refine the model by accounting for confounding effects that may arise during the process.

In some embodiments of the methods described herein, a hidden Markov model is used to determine the most probable copy number state of a segment. The hidden Markov model can include: a hidden layer which comprises the copy number state of a segment of interest; an observation layer, which comprises the mapped number of sequencing reads; a transition probabilities between the copy number state in the hidden layer and mapped number of sequencing reads (probability inter-layers); and a transition probabilities of a copy number state of a segment given the copy number state of a preceding adjacent segment (probability intra-hidden layer). FIG. 1 illustrates one embodiment of a method for determining a copy number of an interrogated segment within a region of interest. At step 110, sequencing reads generated for a test sequencing library are mapped to a segment or segments within a region, or regions of interest. At step 120 the number of sequencing reads mapped at the segment(s) within region(s) of interest is determined. At step 130 a copy number likelihood model is determined which is used to set the transition probability of a copy number state given the observed number of mapped sequencing reads. At step 140, a hidden Markov model is built which comprises the hidden layer, the observation layer and transition probabilities. At step 150 the hidden Markov model is parameterized. In its simplest form, the hidden Markov model comprises at least two unknown parameters: the copy number state and the transition probabilities between the copy number state and observed number of sequencing reads, which are determined by the copy number likelihood model. Expectation-Maximization is used to determine these parameters based on the best fit of the data (that is, parameterize the model) and to determine the most probable copy number. In the model it is desirable to maximize the probability of a copy number state given the observed number of sequencing reads, to determine the most probable copy number of the segment. In step 160 a most probable copy number state of the segment is determined. The process may consider other variables that affect the observation states, such as GC content bias, spuriosity of a capture probe associated with a segment, noisy test sequencing libraries which affect the transition probabilities. The additional variables are treated as latent and determined by EM given the available data. The transition probabilities are then adjusted to account for these other variables. The EM process can be cumulative (adjusting for all variables at once) or it can adjust for the variables in separate EM iterations before the HMM is solved to determine a most probable copy number state of the segment.

Determining a Number of Mapped Sequencing Reads

In some embodiments, the methods described herein include mapping a plurality of sequencing reads generated from a test sequencing library to an interrogated segment. In some embodiments, the methods described herein include mapping a plurality of sequencing reads generated from a test sequencing library to a plurality of spatially adjacent segments, wherein the plurality of spatially adjacent segments includes the interrogated segment. The sequencing library is enriched for a region of interest, such as by direct targeted sequencing. The mapped sequencing reads can be counted to determine a number of sequencing reads that are mapped to the interrogated segment or the spatially adjacent segments.

The spatially adjacent segments are located within the same chromosome. In some embodiments, the spatially adjacent segments are located within the same chromosome region. In some embodiments, the spatially adjacent segments are located within the same gene. In some embodiments, the spatially adjacent segments are located within the same region of interest. In some embodiments, the spatially adjacent segments are located within the same portion within the region of interest.

The sequencing library can be sequenced to generate the plurality of sequencing reads, which can be mapped to a region of interest. The sequencing library includes a plurality of nucleic acid fragments, which can be isolated from bodily fluids such as blood, plasma, saliva, urine or from tissue or cultured cells. The nucleic acid fragments can be from an animal. The nucleic acid fragments can be from a mammal, for example, from a human. In a preferred embodiment the test sequencing library includes a plurality of nucleic acid fragments isolated from a patient. The nucleic acid molecules in the sequencing library can be ligated to sequencing adapters, which may aid alignment in certain sequencing methods. For example the adapters may be indexed, and the indexing may be used to aid alignment of the sequences. The sequencing library can be enriched (such as through direct targeted sequencing) for the region of interest, either before or after ligating the nucleic acid molecules to the sequencing adapters.

The nucleic acid fragments in the test sequencing library may be RNA or DNA nucleic acid fragments. The nucleic acid fragments may be cell-free DNA. In some embodiments, the cell-free DNA comprises fetal cell-free DNA. In some embodiments, the cell-free DNA comprises circulating tumor cell-free DNA.

The nucleic acid fragments in the sequencing library include the region of interest. The region of interest can be a full genome or any portion of the genome. In some embodiments the region of interest comprises one or more chromosomes. In some embodiments the region of interest comprises one or more genes of interest (such as 2 or more, 3 or more, 4 or more, 5 or more, about 10 or more, about 15 or more, about 20 or more, about 30 or more, about 40 or more, about 50 or more, about 75 or more, about 100 or more, about 150 or more, about 200 or more, about 250 or more genes, about 300 or more, about 350 or more, about 400 or more, about 450 or more, about 500 or more, about 550 or more, about 600 or more, about 650 or more, about 700 or more, about 750 or more, about 800 or more, about 850 or more, about 900 or more, about 950 or more, or about 1000 or more). The one or more genes of interest may be any gene associated with a disease. The one or more genes of interest may include any gene associated with a hereditary disease. The one or more genes of interest may include a gene associated with a form of cancer, such as a hereditary cancer. In some embodiments, the region of interest comprises one or more exons (such as 2 or more, 3 or more, 4 or more, 5 or more, 10 or more, 15 or more, 20 or more, 30 or more, 40 or more, 50 or more, 75 or more, 100 or more, 150 or more, 200 or more, or 250 or more, 500 or more, 1000 or more, or 2000 or more exons). In some embodiments, the region of interest comprises a gene or a portion of a gene, an exon, or a portion of an exon, selected from the group consisting of APC, ATM, BARD1, BMPR1A, BRCA1, BRCA2, BRIPI, CDH1, CDK4, CDKN2A, CHEK2, EPCAM, GREM1, MEN1, MLH1, MRE11A, MSH2, MSH6, MUTYH, NBN, PALB2, PMS2, POLD1, POLE, PTEN, RAD50, RAD51C, RAD51D, RET, SDHA, SDHB, SDHC, SMAD4, STK11, TP53, VHL, PEX10, MTHFR, ALPL, HMGCL, DHDDS, PPT1, MPL, WACHC, POMGNT1, CPT2, ALG6, RPE65, ACADM, DPYD, AGL, SLC35A3, DBT, PHGDH, CTSK, NTRK1, NPHS2, LAMC2, LAMB3, USH2A, PHYH, ERCC6, PCDH15, LIPA, HOGA1, OAT, TH, HBB, SMPD1, TPP1, KCNJ11, ABCC8, USH1C, RAG2, RAPSN, TMEM216, PYGM, BBS1, PC, TCIRG1, CPT1A, DHCR7, MYO7A, MED17, PTS, SLC37A4, HYLS1, PFKM, BBS10, GNPTAB, PAH, MMAB, ACADS, PUS1, GJB2, GJB6, SGCG, SACS, ATP7B, CLN5, PCCA, ZFYVE26, VSX2, NPC2, GALC, SERPINA1, VRK1, TECPR2, SLC12A6, IVD, CAPN3, CLN6, NR2E3, HEXA, MPI, FAH, MESP2, BLM, GNPTG, MEFV, PMM2, CLN3, BBS2, TAT, CYBA, FANCA, VPS53, ASPA, CTNS, ACADVL, ALDH3A2, PEX12, NAGLU, G6PC, SGCA, MKS1, DNAI2, GALK1, GAA, SGSH, NPC1, LAMA3, LOXHD1, MCOLN1, MAN2B1, GCDH, NPHS1, BCKDHA, OPA3, FKRP, HADHA, LRPPRC, FAM161A, ATP6V1B1, DYSF, ALMS1, NEB, CERKL, CPS1, BCS1L, CYP27A1, COL4A4, COL4A3, AGXT, NDUFAF5, ADA, RTEL1, HLCS, CBS, AIRE, TRAMU, MLC1, TYMP, ARSA, SUMF1, XPC, BTD, GLBLAMT, GBE1, HGD, PCCB, HPS3, CLRN1, BCHE, ID UA, EVC2, EVC, SEPSECS, SGCB, MTTP, BBS12, MMAA, AGA, F11, NDUFS6, DNAH5, NDUFS4, ERCC8, HEXB, HSD17B4, SLC22A5, SLC26A2, SGCD, PROP1, ADAMTS2, PEX6, MUT, PKHD1, EYS, SLC17A5, BCKDHB, RARS2, LAMA2, ARG1, PEX7, ASL, PEX1, SAMD9, ASNS, SLC26A4, DLD, CFTR, CLN8, STAR, HGSNAT, TTPA, PEX2, CNGB3, VPS13B, CYP11B1, CYP11B2, GLDC, DNAI1, GALT, RMRP, GNE, GRHPR, VPS13A, FANCC, XPA, ALDOB, FKTN, IKBKAP, ASS1, RS1, NR0B1, DMD, OTC, IL2RG, ATP7A, CHM, GLA, COL4A5, IDS, MTM1, ABCD1, or a combination thereof.

The region of interest can be divided into a plurality of segments. Each segment can be further divided into sub-segments. A sub-segment may be 1 or more nucleotides in length. The segments within the region of interest may be but need not be contiguous. For example, in some embodiments, the region of interest comprises 1 or more non-contiguous segments, 2 or more non-contiguous segments, 3 or more non-contiguous segments, 4 or more non-contiguous segments, 5 or more non-contiguous segments, 10 or more non-contiguous segments, 25 or more non-contiguous segments, 50 or more non-contiguous segments, 100 or more non-contiguous segments, 150 or more non-contiguous segments, 200 or more non-contiguous segments, 250 or more non-contiguous segments, 300 or more non-contiguous segments, 350 or more non-contiguous segments, 400 or more non-contiguous segments, 450 or more non-contiguous segments, 500 or more non-contiguous segments, 550 or more non-contiguous segments, 600 or more non-contiguous segments, 650 or more non-contiguous segments, 700 or more non-contiguous segments, 750 or more non-contiguous segments, 800 or more non-contiguous segments, 850 or more non-contiguous segments, 900 or more non-contiguous segments, 950 or more non-contiguous segments, or 1000 non-contiguous segments. In some embodiments, each of the non-contiguous segments comprises 1 or more contiguous bases, 2 or more contiguous bases, 3 or more contiguous bases, 4 or more contiguous bases, or 5 or more contiguous bases. For example, in some embodiments each of the non-contiguous segments comprises 1 to about 20 contiguous bases (such as 1 to about 10 contiguous bases, or about 1 to about 5 contiguous bases). In some embodiments the region of interest comprises 1 or more contiguous segments, 2 or more contiguous segments, 3 or more contiguous segments, 4 or more contiguous segments, 5 or more contiguous segments, 10 or more contiguous segments, 25 or more contiguous segments, 50 or more contiguous segments, 100 or more contiguous segments, 150 or more contiguous segments, 200 or more contiguous segments, 250 or more contiguous segments, 300 or more contiguous segments, 350 or more contiguous segments, 400 or more contiguous segments, 450 or more contiguous segments, 500 or more contiguous segments, 550 or more contiguous segments, 600 or more contiguous segments, 650 or more contiguous segments, 700 or more contiguous segments, 750 or more contiguous segments, 800 or more contiguous segments, 850 or more contiguous segments, 900 or more contiguous segments, 950 or more contiguous segments, or 1000 contiguous segments. In some embodiments, each of the contiguous segments comprises 1 or more contiguous bases, 2 or more contiguous bases, 3 or more contiguous bases, 4 or more contiguous bases, or 5 or more contiguous bases. For example, in some embodiments each of the non-contiguous segments comprises 1 to about 20 contiguous bases (such as 1 to about 10 contiguous bases, or about 1 to about 5 contiguous bases). In some embodiments the region of interest comprises a combination of non-contiguous and contiguous segments. In some embodiments, the region of interest comprises only one segment. In some embodiments the region of interest comprises at least one segment. In some embodiments the region of interest comprises at least two segments. In some embodiments the region of interest comprises at least two segments which are adjacent. In some embodiments one segment within a first region of interest may be adjacent to a segment in a second region of interest adjacent to the first region of interest.

The region of interest may be enriched with one or more capture probes. The reference location of the capture probes with respect to a region of interest is known. For example, the capture probes comprise a reference sequence that corresponds to pre-determined probe coordinates. In some embodiments the region of interest is divided into segments based on the location of capture probes (that is the capture probe corresponds with a segment). The capture probe comprises the reference sequence that corresponds to the probe coordinates. For example, the first nucleotide of a segment may coincide with the first nucleotide of a sequence hybridizing to the 3' end of a capture probe. In some embodiments the first nucleotide of a segment coincides with the first nucleotide of a sequence hybridizing to the 5' end of a capture probe. In some embodiments the region of interest comprises two spatially adjacent segments. A segment within a region of interest may be divided into sub-segments. A sub-segment may be as small as one nucleotide can be as long as the segment. Sub-segments may overlap. For example a first sub-segment may be the first nucleotide of a segment plus one downstream nucleotide. A second sub-segment may comprise the first sub-segment plus an additional downstream nucleotide. In some embodiments, a segment of n nucleotides of length comprises n−1 sub-segments, wherein each subsequent sub-segment is 1 nucleotide longer than the previous. In some embodiments a segment of n nucleotides of length comprises n subsegments, wherein each sub-segment is 1 nucleotide in length.

The region of interest comprises at least one interrogated segment. The interrogated segment is a segment for which it is desirable to know the copy number. The copy number state of an interrogated segment is an unknown state and solving the hidden Markov model determines the most probable copy number of an interrogated segment. Like other segments, an interrogated segment may be divided into sub-segments. In some embodiments the first nucleotide of an interrogated segment coincides with the first nucleotide of a sequence hybridizing to the 5' end of a capture probe. In some embodiments the first nucleotide of an interrogated segment coincides with the first nucleotide of a sequence hybridizing to the 3' end of a capture probe. In some embodiments the interrogated segment comprises the sequence spanning two spatially adjacent capture probes. In a preferred embodiment the interrogated segment comprises the nucleotide sequence between two adjacent capture probes, with the first nucleotide of the sequence being the first nucleotide hybridizing to the 5' end or the 3' end of the capture probe and the last nucleotide of the segment being contiguous to the first nucleotide hybridizing to the 5' end or the 3' end of a spatially adjacent probe.

The test sequencing library can be sequenced using next generation sequencing to generate the sequencing reads. Next generation sequencing technologies are well known in the art. The test sequencing library can be sequenced using a high-throughput sequencer, such as an Illumina HiSeq2500, Illumina HiSeq3000, Illumina HiSeq4000, Illumina HiSeqX, Roche 454, PacBio Sequel System PacBio RS II, or Life Technologies Ion Proton sequencing systems can also be used. Other methods of sequencing are known in the art.

In some embodiments, the sequencing library is enriched with one or more capture probes by direct targeted sequencing. In direct targeted sequencing, capture probes hybridize specific target regions of nucleic acid molecules from within a sequencing library. This method enables enrichment of target regions and allows subsequent sequencing efforts to focus on relevant genomic regions or transcripts of interest. Enriching the target regions with capture probes for the region of interest allows for more efficient high throughput sequencing of the region of interest. The efficiency keeps the overall costs of sequencing test sequencing libraries down while maintaining or increasing the sensitivity and specificity of a diagnostic test or screen. The capture probes can be selected based on the region of interest such that those nucleic acid molecules in the sequencing library containing a portion of the region of interest hybridize to the capture probes and can be enriched, whereas those nucleic acid molecules in the sequencing library that do not contain a portion of the region of interest do not hybridize to the capture probes and are not enriched.

In direct targeted sequencing, capture probes that hybridize to a target sequence adjacent to the corresponding segment within the region of interest are combined with the sequencing library, thereby hybridizing the capture probes to the nucleic acid molecules comprising to the target sequence. In direct targeted sequencing methods, the capture probe is extended using the nucleic acid molecule as a template, and the extended capture probe is sequenced. Since the extended capture probe (or amplified copies of the extended capture probe) itself is sequenced, the sequence of the capture probe is not interpreted as the sequence arising from the test sequencing library, although it can be used to aid sequence alignment.

Other methods for enriching sequencing libraries using capture probes are generally known in the art, and can include hybrid capture techniques (e.g., using biotinylated capture probes), and PCR amplification using capture probes as PCR primers.

In some embodiments, hybrid capture techniques are used to enrich the region of interest by combining capture probes that are substantially complementary to a portion of the region of interest with the sequencing library, thereby hybridizing the capture probes to nucleic acid molecules comprising the portion of the region of interest. The nucleic acid molecules that hybridize to the capture probes can be isolated from non-hybridized nucleic acid molecules (for example, by pull-down methods). The hybridized complex can be denatured and the enriched nucleic acid molecules from the sequencing library can be sequenced. In some embodiments, the enriched nucleic acid molecules are re-enriched in a second (or more) round of hybridization to the capture probes, isolation and denaturation before being sequenced. Optionally, the nucleic acid molecules in the sequencing library can be amplified (for example, by PCR) either before or after enrichment.

In some embodiments, one or more of the capture probes are attached to an additional oligonucleotide (such as a primer binding site or other specialized nucleic acid segment). In some embodiments, the capture probes in the capture probe library are DNA oligonucleotides, RNA oligonucleotides, or a mixture of DNA oligonucleotides and RNA oligonucleotides. In some embodiments the capture probes are about 10-100 bases in length. In some embodiments the capture probes are about 20-60 bases in length. In some embodiments the capture probes are about 30-50 bases in length. In some embodiments the capture probes are 40 bases in length.

The number of capture probes in the capture probe library can depend on the size of the region of interest, as a larger region of interest generally requires a larger number of capture probes for adequate coverage. In some embodiments, the capture probe library comprises about 10 or more unique capture probes (such as about 50 or more, about 100 or more, about 250 or more, about 500 or more, about 1000 or more, about 2500 or more, about 5000 or more, about 10,000 or more, about 25,000 or more, about 50,000 or more, about 100,000 or more, or about 200,000 or more) unique capture probes.

Sequencing the enriched sequencing library generates a plurality of sequencing reads. In order to determine the sequencing depth for a segment or sub-segment, the number of sequencing reads mapped to that segment is determined. Sequencing reads can be mapped, for example, by aligning the sequencing reads (or a portion of the sequencing reads) to a reference sequence, or by assigning the sequencing read to a segment based on a portion of the sequencing read.

In some embodiments, the sequencing reads are mapped by aligning the sequencing reads (or a portion of the sequencing reads) to a reference sequence. For example, sequencing reads resulting from direct targeted sequencing can include a capture probe portion (that is, the portion of the sequencing read that is attributable to the capture probe itself) and a segment portion (that is, the portion of the sequencing read that is attributable to the segment targeted by and associated with the capture probe). In some embodiments, the segment portion is aligned with the reference sequence, the capture probe portion is aligned with the reference sequence, or the capture probe portion and the segment portion are aligned with the reference sequence. The reference sequence includes the region of interest pre-dived into segments. Therefore, the sequencing reads aligned to the reference sequence can be aligned to a corresponding segment, and the aligned sequencing reads are assigned or "mapped" to that segment.

In some embodiments, the sequencing reads are mapped by assigning the sequencing read to a segment based on a portion of the sequencing read. In such an embodiment, it is not necessary to align the sequencing read to a reference sequence. Because the capture probes each correspond with a segment, and the corresponding segment is known by the design of the capture probe, sequencing reads that contain a sequence of the capture probe (or its complement) can be assigned (or "mapped") to the corresponding segment.

In some embodiments, the sequencing depth may be obtained by determining the sequencing reads mapped to that segment. In some embodiments the sequencing depth may be obtained by determining the sequencing reads mapped to a capture probe corresponding to that segment.

In some embodiments, two or more capture probes overlap (that is, the capture probes can hybridize to overlapping sequences within the region of interest). The two or more capture probes may overlap by about 0%-10%, about 10-20%, about 20%-30%, about 30%-40%, about 40%-50%, about 50%-60%, about 60%-70%, about 70%-80%, about 80%-90%, or about 90%-99% of the length of the probe. In some embodiments, two or more capture probes overlap 100%. In some embodiments, the number of sequencing attributable to two or more capture probes correlate with each other. Overlapping or correlated capture probes can be accounted for by merging (i.e., adding together) the number of sequencing reads attributed to the overlapping or correlated capture probes.

Once the plurality of sequencing reads are mapped to the interrogated segment or a plurality of spatially adjacent segments (including the interrogated segment), the number of sequencing reads mapped to the interrogated segment or the spatially adjacent segments (including the interrogated segment) can be determined by counting the number of sequencing reads that have been assigned to the segment.

Building, Initializing and Maximizing a Copy Number Likelihood Model

The copy number likelihood model may be any statistical model that can be used to determine the likelihood of observing a number of sequencing reads mapped at a segment given the copy number state of the segment. An initial copy number likelihood model refers to the model where the parameters for the model have been defined, but before optimizing it. In a preferred embodiment the copy number likelihood model includes one or more likelihood distributions for an expected number of mapped sequencing reads given a copy number state. That is, each likelihood distribution corresponds to a copy number state. For example the copy number likelihood model may comprise a likelihood distribution of an expected number of sequencing reads given a copy number state of 1, a likelihood distribution of an expected number of sequencing reads given a copy number state of 2, a likelihood distribution of an expected number of sequencing reads given a copy number state of 3, and a likelihood distribution of an expected number of sequencing reads given a copy number state of 4. The copy number likelihood model need not comprise a likelihood distribution for each possible copy number state, but comprises at least one likelihood distribution. Similarly, the copy number likelihood model may comprise distributions for copy number states greater than 4, such as a copy number state of 5, of 6, of 7 or of 8. In some embodiments the distributions comprised in the copy number likelihood model are Poison distributions. In some embodiments the distributions comprised in the copy number likelihood model are binomial distributions. In some embodiments the copy number likelihood model comprises negative binomial distributions. For example, in some embodiments the copy number likelihood model comprises one or more negative binomial distributions (or one or more negative binomial distributions, wherein the negative binomial distribution is not a Poisson distribution) for expected mapped sequencing reads for interrogated segment i in test sequencing library j for copy number states $c_{i,j}$.

The likelihood distribution of the copy number likelihood model can be further characterized by a mean (μ) and a dispersion (d). The mean and the dispersion of the likelihood distribution are optimized by using a determined expected number of sequencing reads, at segment i (that is, using the same capture probe) by sequencing the test sequencing library j at a plurality of segments (that is, using a capture probe library) and by setting a copy number state at the segment i for sequencing library j. The expected number of sequencing reads is based on at least three factors: the average number of mapped sequencing reads for the segment across a plurality of sequencing libraries, the average number of mapped sequencing reads for the test sequencing library across a plurality of segments, and the local copy number state of the segment. The mean of the distribution can be set as: $\mu=c_{i,j}\mu_i\mu_j$ wherein $\mu_i$ is the average number of mapped sequencing reads for segment i across $N_s$ sequencing libraries, $\mu_j$ is the average number of mapped sequencing reads for the test sequencing library j across $N_p$ segments, and $c_{i,j}$ is the copy number state at segment i for test sequencing library j and $k_{i,j}$ is the determined number of sequencing reads at segment i for test sequencing library j.

Formally:

$$\mu_i = \frac{\sum_j k_{i,j}}{N_s}$$

$$\mu_j = \frac{\sum_i k_{i,j}/\mu_i}{N_p}$$

The copy number likelihood model is set by determining distributions from an expected number of sequencing reads for different copy number states then maximized for a most probable $c_{i,j}$ given the number of actual mapped sequencing reads at the segment.

Figure 2A:
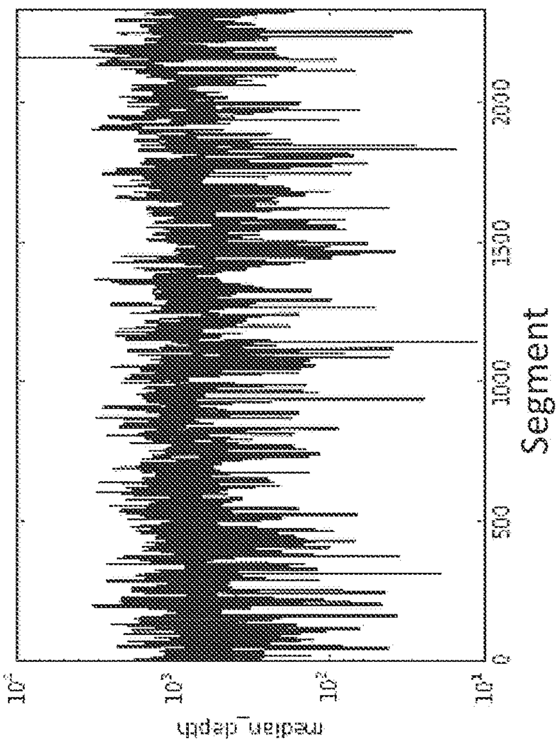
FIG. 2A shows the sequencing read count (i.e., sequencing depth) for across approximately 2500 segments (approximately 2500 unique capture probes) in a single test sequencing library.
Figure 2B:
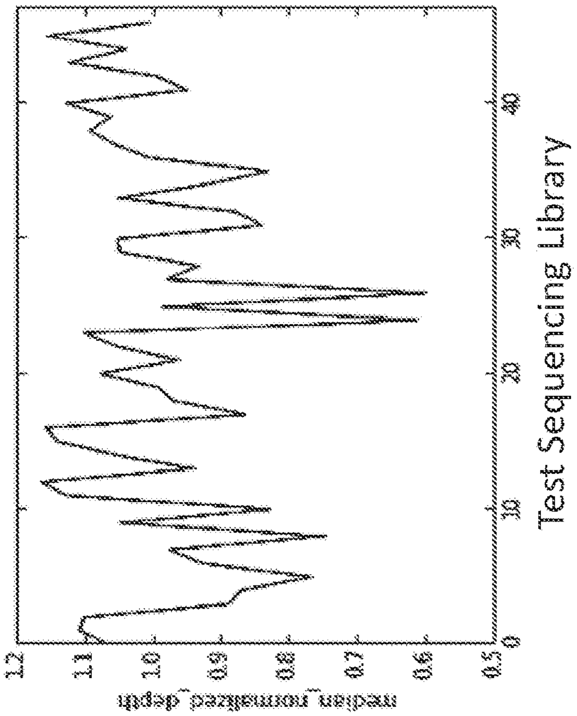
FIG. 2B shows median normalized sequencing depth (that is, the sequencing depth for a single segment normalized to the median for that same segment across all test sequencing libraries) for 48 different test sequencing libraries.

For the majority of genes the expected copy number (i.e., "wild-type") is assumed to be two (i.e., diploid). This is not necessarily always the case. For example, for genes on the Y chromosome the expected copy number (i.e., "wild-type") should be assumed to be 1. Considering this relationship, in some embodiments the copy number likelihood distribution for any given copy number state is centered at an average $$\mu_{c,i,j} = \frac{c}{2}\mu_i\mu_j$$

wherein $\mu_i$ is the average number of mapped sequencing reads for segment i across $N_s$ sequencing libraries, $\mu_j$ is the average number of mapped sequencing reads for the test sequencing library j across $N_p$ segments, and c is the number of copies for the given copy number likelihood distribution, wherein $\mu_i$ is a normalized average number of mapped sequencing reads. The number of mapped sequencing reads for segment i in a given sequencing library can be normalized by dividing the number of mapped sequencing reads at segment i within the sequencing library by the average number of mapped sequencing reads across $N_p$ segments within that sequencing library. FIG. 2A presents an example profile of the number of sequencing reads for approximately 2500 capture probes, wherein the sequencing library was enriched by direct targeted sequencing. FIG. 2B present an example profile of a normalized number of mapped sequencing reads at segment i for approximately 48 different sequencing libraries, wherein the sequencing library was enriched for segment i by direct targeted sequencing.

The copy number likelihood distribution also includes a dispersion (d, estimated for segment i as:

$$d_i = \frac{\mu_i^2}{\sigma_i^2 - \mu_i}$$

wherein $\sigma_i^2$ is the variance of the number of mapped sequencing reads for the plurality of sequencing libraries.

The copy number likelihood distribution can be a Poisson distribution, a binomial distribution, a negative binomial distribution (such as a generalized Poisson negative binomial distribution or a negative binomial distribution the is not a Poisson distribution), or any other suitable distribution. It has been found that a negative binomial distribution, wherein the negative binomial distribution is not a Poisson distribution is particularly useful for determining the copy number likelihood distributions. FIG. 3A shows a plot of the sequencing depth variance against the mean number of sequencing reads ("mean depth") for approximately 2500 capture probes used to enrich a sequencing library for a region of interest for a plurality of different test sequencing libraries. The data was fit using a negative binomial distribution, wherein the negative binomial distribution is not a Poisson distribution. As a comparison, a Poisson distribution is also illustrated, which assumes a linear relationship between dispersion and mean depth. As it can be seen in FIG. 3A, the data violates the Poisson assumption that the mean sequencing depth is equal to the sequencing depth variance, as plotting the data shows that variance is greater than mean. Thus, the data fits a negative binomial distribution significantly better than the Poisson distribution.

FIG. 3B illustrates a copy number likelihood model including a copy number likelihood distribution for a copy number of 1 (CN=1), 2 (CN=2), and 3 (CN=3). FIG. 3B illustrates a Poisson distribution and a negative binomial distribution, wherein the negative binomial distribution is not a Poisson distribution. for each copy number. The distributions are probability mass functions (pmf) as a function of the number of sequencing reads from the capture probe corresponding with the segment.

Building a Hidden Markov Model

A hidden Markov model allows for the determination of a most probable copy number (a hidden state) from the number of mapped sequencing reads (an observation state). Generally, there are four main parameters in the hidden Markov model: one or more hidden states, one or more observation states, one or more emission probabilities from the hidden states to the observation states, and the transition probabilities between the hidden states. Provided herein are methods of building the hidden Markov model and parameterizing the hidden Markov model. Also, provided herein are methods of training the hidden Markov model using an incomplete data set. Also provided herein are methods of optimizing the hidden Markov model by optimizing parameters in the hidden Markov model to account for variables that affect the emission probabilities between the hidden states and the observation states. Specifically, provided below are methods and explanations on the layers of the hidden Markov model; the transition probabilities of the Markov model; the copy number likelihood model; using expectation-maximization to parameterize the hidden Markov model; adjusting the hidden Markov model to account for a number of latent variables; solving the hidden Markov model.

Figure 4A:
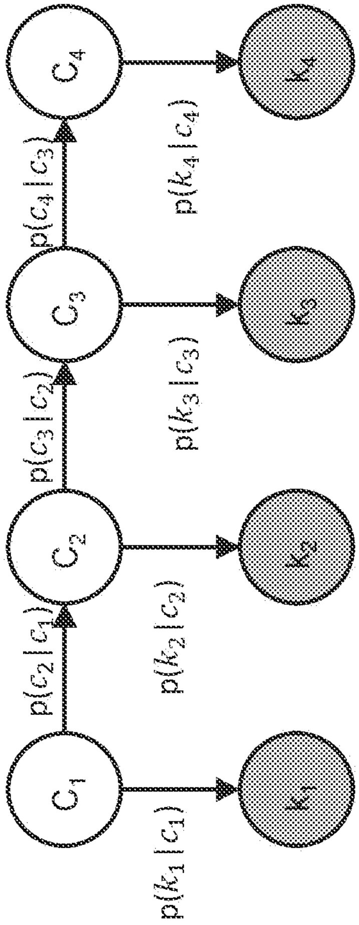
FIG. 4A shows an exemplary hidden Markov model with $c_1$, $c_2$, $c_3$, and $c_4$ represent the hidden states (i.e., the most probable copy number for four different segments) and $k_1$, $k_2$, $k_3$, and $k_4$ represent the observed states (i.e., the number of mapped sequencing reads for each corresponding segment). The probabilities between the observed states and the hidden states at each corresponding segment are indicated by $p(c_1|k_1)$, $p(c_2|k_2)$, $p(c_2|k_2)$, and $p(c_2|k_2)$, while the transition probabilities between the hidden states are indicated by $p(c_2|c_1)$, $p(c_3|c_2)$, and $p(c_4|c_3)$. The copy number likelihood model is used to parameterize the probabilities between the observed states and the hidden states. Both sets of probabilities are optimized using expectation-maximization (EM).

An exemplary hidden Markov model that can be used with the disclosed methods is illustrated in FIG. 4A. In FIG. 4A, $c_1$, $c_2$, $c_3$, and $c_4$ represent the hidden states (i.e., the most probable copy number for four different segments, although it is understood that the model can include n number of segments) and $k_1$, $k_2$, $k_3$, and $k_4$ represent the observed states (i.e., the number of mapped sequencing reads for each corresponding segment). The transition probabilities are the probability of transitioning from a copy number for one segment to a copy number in an adjacent segment, and is represented by $p(c_2|c_1)$, $p(c_3|c_2)$, and $p(c_4|c_3)$. Finally, the probability of a hidden state (i.e., the copy number for the segment) given the observed state (the number of mapped sequencing reads for that segment) is represented by $p(c_1|k_1)$, $p(c_2|k_2)$, $p(c_2|k_2)$, and $p(c_2|k_2)$. The latter is the posterior probability that is solved for. To determine the posterior probability, the copy number likelihood model of $p(k_1|c_n)$ is used.

In some embodiments a hidden Markov model comprises only one hidden state and a corresponding observation state. In some embodiments the hidden state corresponds to the copy number state of a segment and the observation state corresponds to the mapped number of sequencing reads at that segment. In some embodiments the hidden Markov model comprises a plurality of hidden states and a plurality of observation states. In some embodiments the plurality of the hidden states corresponds to the copy number states at a plurality of segments and the plurality of observation states corresponds to the number of mapped sequence reads at the plurality of segments. In some embodiments, each segment within a region of interest corresponds to a capture probe for the region of interest. In some embodiments, two adjacent hidden states correspond to two spatially adjacent segments within the region of interest.

Figure 4B:
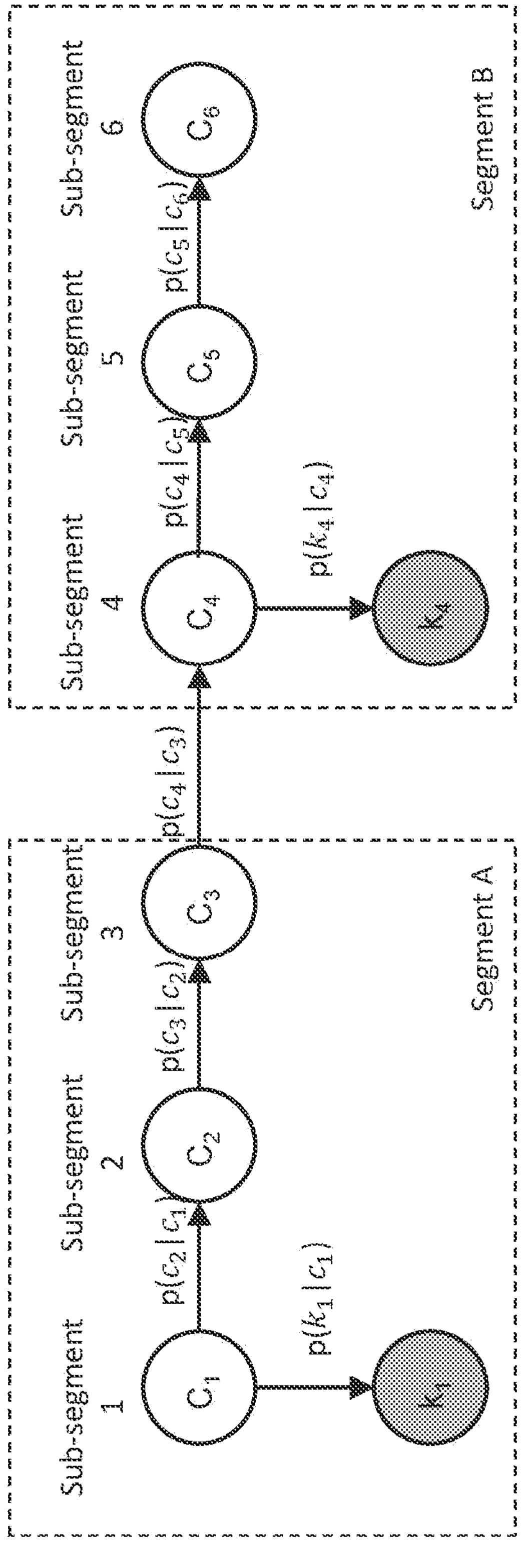
FIG. 4B illustrates a hidden Markov model for two segments subdivided into sub-segments. The sub-segments include hidden states, but do not include observed states. The transition probabilities of a sub-segment based on the copy number state of an adjacent sub-segment. This can be done on a per base (or per sub-segment) segmentation.

The segments may be divided in sub-segments, as previously described herein. In some embodiments the hidden states correspond to the copy number of the sub-segments. The sub-segments do not include a mapped number of sequencing reads independent of the mapped number of sequencing reads for the parent segment (that is, the segment to which the sub-segment is a member). In some embodiments, the mapped number of sequencing reads for the segment is attributed to each sub-segment within the segment. In some embodiments, the sub-segment includes a hidden state (i.e., a copy number), but the mapped number of sequencing reads is only attributed to the first sub-segment of the segment. This is illustrated in FIG. 3B. FIG. 4B includes two segments identified by the dashed lines: Segment A and Segment B. Segment A includes sub-segment 1, sub-segment 2, and sub-segment 3, while Segment B includes sub-segment 4, sub-segment 5, and sub-segment 6. The number of mapped sequencing reads for Segment A is attributed to the first sub-segment in that segment, sub-segment 1. The number of mapped sequencing reads for Segment B is attributed to the first sub-segment in that segment, sub-segment 4. $C_1$, $C_2$, $C_3$, $C_4$, $C_5$, and $C_6$ represent the hidden state (copy number) for each of the sub-segments, and $K_1$ and $K_4$ represent the observed states (number of sequencing reads) for sub-segment 1 and sub-segment 4, respectively. The transition probabilities between the sub-segment hidden states are identified by $p(c_2|c_1)$, $p(c_3|c_2)$, $p(c_4|c_3)$, $p(c_5|c_4)$ and $p(c_6|c_5)$. Because only sub-segment 1 and sub-segment 4 include observation states, only two probabilities for a number of mapped sequencing reads given a copy number of the sub-segment are included: $p(k_1|c_1)$ and $p(k_4|c_4)$.

The copy number state of a segment is related to the number of sequencing reads mapped to that location. Determining a copy number state of a segment or sub-segment (which can be denoted as $c_{i,j}$) given a number of mapped sequencing reads (which can be denoted as $k_{i,j}$) for segment (or sub-segment) i in test sequencing library j allows for calling of a copy number of that segment or sub-segment. The probability for a given copy number state being the correct copy number depends at least on the number of mapped sequencing reads. In Bayesian statistics, the posterior probability of $c_{i,j}$ given $k_{i,j}$ (that is, $p(c_{i,j}|k_{i,j})$) can be determined using a copy number likelihood distribution. While posterior probability is a probability of a parameter given some data; a likelihood model is the probability of the data, given the parameter. In this case, the posterior probability is the probability of the copy number state of a segment or sub-segment given the number of sequencing reads mapped at that segment or sub-segment (that is, $p(c_{i,j}|k_{i,j})$), whereas the copy number likelihood model is the likelihood of observing a number of sequencing reads mapped at a segment given the copy number state of the segment (that is, $p(k_{i,j}|c_{i,j})$). Since $p(c_{i,j}|k_{i,j})$ cannot be directly determined, the copy number likelihood model $p(k_{i,j}|c_{i,j})$ can be used to parameterize the hidden Markov model, which can be used to solve for the posterior probability $p(c_{i,j}|k_{i,j})$. The following discusses the copy number likelihood model as a negative binomial distribution, but it is understood that the similar aspects would apply for other distribution forms. In some embodiments, the copy number likelihood model can be defined as:

$$p(k_{i,j}|c_{i,j})=NegBinom(k_{i,j}|\mu_{c,i,j}=c_{i,j}\mu_i\mu_j;d=d_i)$$

wherein $k_{i,j}$ is the number of mapped sequencing reads at segment i for the test sequencing library j.

The negative binomial distribution is parameterized to best fit the data. In its simplest form the copy number likelihood model is a negative binomial model. However, depending on the data generated, a different type of distribution may fit the data better and may be better suited. The general aspects of this invention would apply to models comprising different statistical distributions.

The transition probability for a copy number of a segment or sub-segment depends, in part, on the copy number state of a spatially adjacent segment or sub-segment. Lengths and frequencies of copy number variants can also impact the transition probabilities.

In some embodiments, the transition probability can be predetermined or fixed. In a preferred embodiment, the transition probability is variable. For example, the transition probability can be formally represented by the following stochastic transition matrix assuming a hidden copy number state limited to 0, 1, 2, 3, or 4 copies (assuming a wildtype copy number of 2):

$$p(C_{i+1}|C_i)=\begin{bmatrix} 1-r_{01} & r_{10} & 0 & 0 & 0 \\ r_{01} & 1-r_{12}-r_{10} & r_{21} & 0 & 0 \\ 0 & r_{12} & 1-r_{23}-r_{21} & r_{32} & 0 \\ 0 & 0 & r_{23} & 1-r_{32}-r_{34} & r_{43} \\ 0 & 0 & 0 & r_{34} & 1-r_{43} \end{bmatrix}$$

wherein $C_i$ is the copy number state of a first segment or first sub-segment; $C_{i+1}$ is the copy number state of the second segment or second sub-segment that is spatially adjacent to the first segment or first sub-segment; and $r_{ab}$ represents the transition probability from a first copy number state a to a second copy number state b. For example, a can be a copy number state of 3 and b can be a copy number state of 2. The first segment can be the interrogated segment (or the first sub-segment can be a sub-segment of the interrogated segment). Although the above stochastic transition matrix assumed 0, 1, 2, 3, or 4 copies, it is understood that a stochastic transition matrix can be used for any number of copies.

Copy number variants have an average length, and copy numbers that are longer or shorter than this length are less likely than copy numbers at the average length. In some embodiments the transition probability (or transition probabilities) account for an average length of a copy number variant. The average length of the copy number variant can be based on observations from a historical population (e.g., a historical human population). The historical population is a historical population of sequencing libraries for which a copy number variant has been called. Larger historical populations can result in more accurate average copy number variant lengths. In some embodiments, the historical population comprises about 1000 or more sequencing libraries (such as about 5000 or more, about 10,000 or more, about 25,000 or more, about 50,000 or more, about 100,000 or more, about 250,000 or more, or about 500,000 or more sequencing libraries). The average length of a copy number variant is predetermined. In some embodiments, the average length of a copy number variant is about 3000 to about 1000 bases (such as about 4000 to about 8000 bases, about 5000 to about 7000 bases, about 5500 bases to about 6500 bases, or about 6200 bases). Accounting for the average length of a copy number, the transitions in the stochastic transition matrix which is used to calculate the per base transition probability (or sub-segment transition probability can be set as:

$$r_{01}=r_{12}=r_{32}=r_{43}=\frac{1}{\langle l\rangle_{CNV}}$$

wherein $\langle l\rangle_{CNV}$ is the average length of a copy number variant.

The transition probabilities can also account for the probability of a copy number variant at the interrogated segment given the copy number state at a spatially adjacent segment. Certain portions of the genome may include "hot spots" of genetic variation, including copy number variation. Hot spots, refers to regions in the genome which display a high propensity for mutations of all kinds. This might be due to structural makeup of the region, or functional aspects of the region, which make it more prone to mutations. The probability of a copy number variant at any given segment (such as an interrogated segment or a spatially adjacent segment) can be based on observations from a historical population (e.g., a historical human population). The historical population is a historical population of sequencing libraries for which a copy number variant has been called. Larger historical populations can result in more accurate copy number variant probabilities. In some embodiments, the historical population comprises about 1000 or more sequencing libraries (such as about 5000 or more, about 10,000 or more, about 25,000 or more, about 50,000 or more, about 100,000 or more, about 250,000 or more, or about 500,000 or more sequencing libraries). To account for the probability of a copy number variant at the interrogated segment or a spatially adjacent segment, the transitions in the stochastic transition matrix can be set as:

$$r_{21} = r_{12}\frac{p_{CNV}}{1 - 2p_{CNV} - 2p_{CNV}^2}$$

wherein $p_{CNV}$ is the probability of a copy number variant. Since $r_{01}=r_{12}=r_{32}=r_{43}$ the relationship described holds true for all copy numbers.

In some embodiments, the hidden Markov model comprises one transition probability of a copy number state of a segment or of a sub-segment. In some embodiments, the hidden Markov model comprises a plurality of transition probabilities of a copy number state of a segment or of a sub-segment. In some embodiments, the transition probability of a copy number state given the copy number state of an adjacent preceding segment is dependent on length of a copy number variant. In some embodiments, the length of the copy number variant is specific for that particular region of the genome. In some embodiments, the length of a copy number variant is the average length of a copy number variant across the genome.

In some embodiments the transition probability of a copy number state given the copy number state of an adjacent preceding segment is dependent on the probability of observing a copy number variant. In some embodiments the probability of observing a copy number variant is specific for that particular region of the genome. In some embodiments the probability of observing a copy number variant is the average probability of observing a copy number variant across the genome.

Parameterizing the Hidden Markov Model and Determining a Most Probable Copy Number As described above, the hidden Markov model includes (i) one or more hidden states comprising a copy number corresponding to the one or more segments or sub-segments (including at least the interrogated segment or a sub-segment of the interrogated segment), (ii) one or more observation states comprising the number of sequencing reads mapped to the one or more segments, and (iii) the copy number likelihood model. The copy number likelihood model is used to describe the probability of observing an observation state for a given hidden state (that is, $p(k_{ij}|c_{i,j})$). The hidden Markov model also includes a transition probability between the hidden states, which can be fixed or variable as described above.

The hidden Markov model is initiated using the copy number likelihood model. The hidden Markov model can also be initiated by assuming the copy number state (i.e., the hidden state) to have a wild-type number of copies (for example, two copies), which can be used to back-calculate the transitions (r) for determining the transition probabilities. The copy number likelihood model is based on the expected number of sequencing reads mapped to the segment, as explained above, but the copy number likelihood model can be adjusted to fit the determined number of sequencing reads mapped to the segment (i.e., the observed states), for example by allowing the mean $\mu_{c,i,j}$ and dispersion $d_i$ for each copy number likelihood distribution in the copy number likelihood model to float when parameterizing the hidden Markov model. The transition probabilities, if variable, can also be adjusted during parameterization of the hidden Markov model.

Parameterization of the hidden Markov model includes adjusting the copy number likelihood model to fit the determined number of sequencing reads mapped to the segment (e.g., the interrogated segment or the spatially adjacent segments). In some embodiments, the copy number likelihood model is optimized to fit the determined number of sequencing reads mapped to the segment (e.g., the interrogated segment or the spatially adjacent segments). The copy number likelihood model is "optimized" after a plurality of adjustment rounds to best fit the observed states. In some embodiments, parameterization of the hidden Markov model includes adjusting (or optimizing) the transition probabilities. The hidden Markov model can be optimized by a collection of useful algorithms known in in the art, such as the class of Expectation-Maximization (EM) algorithms (including the Baum-Welch algorithm, which includes alpha-beta recursion), a Viterbi algorithm, a Quasi-Newton solver, or a Markov chain Monte Carlo.

For example, expectation-maximization (EM) may be used to adjust (or optimize) the copy number likelihood model (based on the expected number of sequencing reads) to find a maximized expected sequencing reads mapped to the segment (that is, an adjusted $\mu_{c,i,j}$) and an adjusted dispersion for that segment (that is, an adjusted $d_i$). That is, so that the probability of an expected number of sequencing reads at an interrogated segment is maximized for a given copy number state at that segment.

Generally, expectation-maximization (EM) can be used to estimate latent, or unknown parameters despite incomplete data. The EM algorithm can iteratively alternate between the expectation "E" step which selects a most likely copy number likelihood distribution from the copy number likelihood model given the determined number of sequencing reads mapped to the segment (such that the most probable copy number can be determined), and a maximization "M" step, which re-estimates the copy number likelihood model parameters (i.e., $\mu_{c,i,j}$ and $d_i$). The Maximization step assumes a fixed probabilistic model and number of sequencing reads, and then finds the copy number state that would, when applied to the model, result into a highest probability for the actual number of mapped sequencing reads out of all other possible copy numbers. An EM process can be applied at different parameters of the HMM, for example it can consider the transitions (r) between the hidden states if applicable, using the expectations generated in the "E" step. Simplistically, the EM is used to maximize the model so that we find for which $c_{i,j}$ are we most likely to see the number of mapped sequencing reads that we observed. Formally, a Vitterbi algorithm can determine the maximum likelihood for the copy number likelihood model as:

$$c_{i,j}^* = \underset{c_{i,j}}{\operatorname{argmax}}\, p(k_{i,j} \mid c_{i,j})$$

In some embodiments, a Baum-Welch algorithm is used to parameterize the hidden Markov model. The Baum-Welch algorithm uses a posterior probability $\alpha(c_i|k_{[0,i]})$, which is the probability of a copy number state at segment i for a given number of mapped sequencing reads at segment i, and a likelihood $\beta(k_{[i,I]}|c_i)$, which is the probability of the number of mapped sequencing reads for the downstream spatially adjacent segments i to I for a given copy number state at segment i. The Baum-Welch algorithm can be solved using methods known by a person of skill in the art.

The parameterized hidden Markov model can be used to determine a most probable copy number of the interrogated segment or a sub-segment of the interrogated segment during the Maximization step. The most probable copy number of the interrogated segment can be determined using any useful algorithm known in the art, such as a Viterbi algorithm, a Quasi-Newton solver, or a Markov chain Monte Carlo.

GC Content Bias Correction

GC content of a segment of the region of interest or a capture probe corresponding to the segment can affect the number of sequencing reads mapped to the segment, for example due to differences in hybridization efficiency of the capture probe. Thus, depending on GC content, a capture probe may have strong effects on the number of sequencing reads mapped to a segment, irrespective of the copy number state at that segment. This GC content bias is well known and described in the art. In some embodiments of the methods described herein, the GC content bias is accounted for when determining a copy number of the segment. The GC content bias correction can be useful in any method of determining a copy number variant, and need not be used solely with direct targeted sequencing. For example, in some embodiments, GC content bias is corrected when determining a copy number of a segment in a region of interest, wherein the sequencing library is enriched using hybrid capture techniques. Additionally, the methods for correcting GC content bias need not be limited to methods using a hidden Markov model to determine a copy number, but the GC content bias can be corrected for any method that includes the use of a copy number likelihood model.

In some embodiments, a number of sequencing reads (such as the expected number of sequencing reads used to determine the copy number likelihood model) for any given segment is corrected for GC content by multiplying the number of sequencing reads by a GC bias correction factor. The GC bias correction factor is specific for the given segment and for the test sequencing library. That is, the GC bias correction factor is uniquely determined for the segment and the test sequencing library, and the GC bias correction factor must be re-determined for a different segment and for each different test sequencing library.

The number of sequencing reads mapped to a given segment (which may include the interrogated segments) can be normalized by dividing the number of mapped sequencing at that segment by the average number of mapped sequencing reads for a plurality of segments enriched from the test sequencing library. The normalized number of sequencing reads for each segment within the plurality of segments can be plotted against the GC content at that segment. The data points can then be fit using a second order correction:

$$k_{N,j}=a+b(GC)+c(GC)^2$$

wherein $k_{N,j}$ is the normalized number of sequencing reads specific for test sequencing library j for the plurality of segments, (GC) is the GC content, and a, b, and c are constants determined by the second order fit.

The GC bias correction factor can therefore be determined by fitting a second order function to a plurality of data points, wherein the data points each comprises a normalized number of sequencing reads mapped to a segment and the GC content of that segment, and wherein the plurality of data points represent a plurality of segments enriched by the capture probes in the test sequencing library; and defining the GC bias correction factor to be the normalized number of sequencing reads determined by the second order function for the GC content of the segment.

The copy number likelihood model can be adjusted to account for the presence of GC content bias in a similar manner. That is, the expected number of sequencing reads used as a basis for the copy number likelihood model can be adjusted to account for the presence of GC content. For example, the average of the copy number likelihood distribution in the model can be adjusted such that:

$$\mu_{c,i,j}=c_{i,j}\mu_i\mu_j k_{i,j}$$

Further, the copy number likelihood model can be formalized as:

$$p(k_{i,j}|c_{i,j})=NegBinom(k_{i,j}|\mu_{c,i,j}=c_{i,j}\mu_i\mu_j k_{i,j}, d=d_i)$$

In some embodiments, there is a method for determining a copy number of an interrogated segment or a sub-segment of the interrogated segment within a region of interest comprising: (a) mapping a plurality of sequencing reads generated from a test sequencing library to a segment within a region of interest, wherein the test sequencing library is enriched using a capture probe; (b) determining a number of sequencing reads mapped to the segment; (c) determining a copy number likelihood model for the segment based on an expected number of mapped sequencing reads at the segment, wherein the expected number of mapped sequencing reads is corrected for GC content of the segment; and (d) determining a most probable copy number of the interrogated segment based on the copy number likelihood model. The most probable copy number of the interrogated segment can be determined based on the copy number likelihood model using the hidden Markov model described herein, or can be done by any other method known in the art. For example, the most probable copy number can be determined based on the maximum copy number probability of each region based on a capture probe for that region. In another example, the most probable copy number can be determined using a brute force segmentation approach.

In some embodiments, there is a method for determining a copy number of an interrogated segment or a sub-segment of the interrogated segment within a region of interest comprising: (a) mapping a plurality of sequencing reads generated from a test sequencing library to the interrogated segment, wherein the test sequencing library is enriched using one or more capture probes; (b) determining a number of sequencing reads mapped to the interrogated segment; (c) determining a copy number likelihood model based on an expected number of sequencing reads mapped to the interrogated segment, wherein the expected number of mapped sequencing reads is corrected for GC content of the interrogated segment; (d) building a hidden Markov model comprising: (i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model; (e) parameterizing the hidden Markov model by adjusting the copy number likelihood model to fit the determined number of sequencing reads mapped to the interrogated segment; and (f) determining a most probable copy number of the interrogated segment or a sub-segment of the interrogated segment based on the parameterized hidden Markov model.

In some embodiments there is a method for determining a copy number of an interrogated segment or a sub-segment of the interrogated segment within a region of interest comprising: (a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent capture probes; (b) determining a number of sequencing reads mapped to each spatially adjacent segment; (c) determining a copy number likelihood model for each spatially adjacent segment based on an expected number of mapped sequencing reads at the spatially adjacent segment, wherein the expected number of mapped sequencing reads is corrected for GC content of the spatially adjacent segment; (d) building a hidden Markov model comprising: (i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; (e) parameterizing the hidden Markov model comprising adjusting each copy number likelihood model to fit the determined number of sequencing reads mapped to each spatially adjacent segment; and (f) determining a most probable copy number of the interrogated segment or a sub-segment of the interrogated segment based on the parameterized hidden Markov model.

Spurious Capture Probes

Certain capture probes used to enrich a segment within the region of interest can produce spurious results. For example, the number of sequencing reads generated by a spurious capture probe may not be consistent with the copy number of a corresponding segment, either by under or over enriching the segment. These spurious results can occur, for example, due to capture probe design or sequence variants (e.g., SNPs) within the sequence the capture probe was designed to hybridize to. Spurious capture probes affect number of mapped sequencing reads and can artificially confound the copy number likelihood model and parameters. It is therefore desirable to account for spurious capture probes. Spurious capture probes need not be direct targeted sequencing capture probes, and similar methods can be applied to capture probes used to enrich a test sequencing library (such as by hybrid capture techniques). The determination of whether a capture probe is a spurious capture probe can be made using EM. For example, the determination of whether the capture probe is spurious can be made during the expectation step, and when the probability of a capture probe being spurious changes during EM iterations, so will the maximization step, which in turn determines the most likely copy number state of the segment which now takes into consideration the spuriosity of the capture probe. If a capture probe is determined to be a spurious capture probe, the probability of the number of mapped sequencing reads for a segment for a copy number state is set to 1 during the expectation-maximization process. By setting it a constant it effectively allows the model to disregard the spurious capture probe as it provides no additional information and is thus not taken into consideration as the model is parameterized. Determination of the spuriousness of the capture probe can be iterative, for example by determining whether the capture probe is spurious after a number of EM cycles.

In some embodiments a Bernoulli process is used to determine the probability that a given capture probe is spurious. The Bernoulli process can be applied to some or all of the capture probes. That is, for each capture probe its spuriosity is independently determined. For capture probe i, an indicator variable $b_i$ is introduced where 1 means that the capture probe t is spurious and 0 means that the capture probe is not spurious.

$$b_i \in \{0,1\}$$

By using this indicator, it is possible to account for spurious capture probes by adjusting the copy number likelihood model. If a capture probe is determined to be spurious, the probability of a number of mapped sequencing reads for the corresponding segment for any given copy number is set to 1. If the capture probe is non-spurious, the copy number likelihood distributions in the copy number likelihood model are unchanged. Formally:

$$p(k_{i,j} \mid c_{i,j}, b_i) = \begin{cases} 1 & \text{if } b_i = 1 \\ NegBinom(k_{i,j} \mid c_{i,j}; \mu_{c,i,j}; d_i) & \text{if } b_i = 0 \end{cases}$$

Figure 5A:
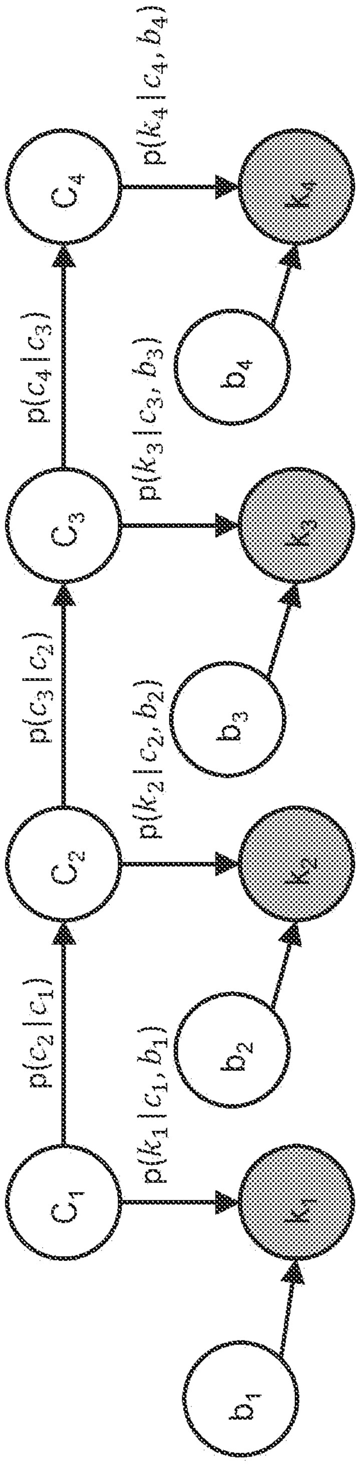
FIG. 5A illustrates a hidden Markov model, wherein a spurious capture probe indicator prior is placed on the observation state.

The indicator on the observed states of the hidden Markov model is illustrated in FIG. 5A.

The spuriousness of capture probes may depend on the test sequencing library. That is, some test sequencing libraries may be more prone to spurious capture probes than other test sequencing libraries. In some embodiments whether a test sequencing library is prone to spurious capture probes is determined based on test sequencing library priors. In some embodiments determining whether a test sequencing library will be prone to a particular probe being spurious depends on a general prior.

Figure 5B:
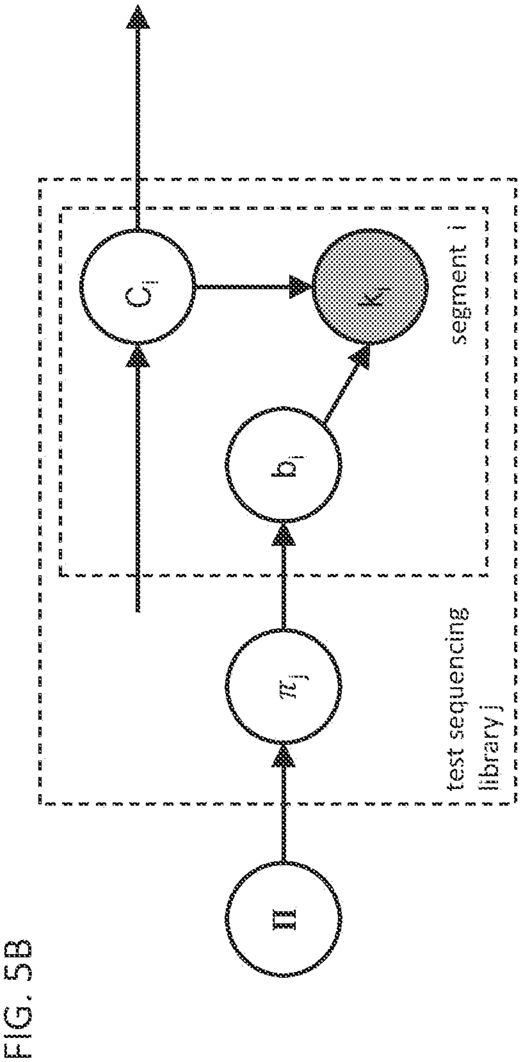
FIG. 5B illustrates priors that can be adjusted to determine if a given capture probe is a spurious capture probe, which is used to determine the prior $b_i$ on the observed state $k_i$. A Bernoulli process can be used to determine the spurious capture probe probability for each test sequencing library and how this probability can influence the spuriosity of probes for that test sequencing library.

FIG. 5B illustrates priors that can be adjusted to determine if a given capture probe is a spurious capture probe. The indicator variable $b_{i,j}$ is a Bernoulli distribution prior on $k_i$, the observation state (the number of mapped sequencing reads) of segment i. The indicator variable $b_{i,j}$ may be specific for the segment i and for test sequencing library j. A test sequencing library prior $\pi_j$ is set on the indicator variable $b_t$, and is the same across all segments within the region of interest of the test sequencing library. A general prior Π is set on the test sequencing library prior $\pi_j$, and is the same for all sequencing libraries similarly enriched. The general prior Π can be pre-determined, and validated to reduce false calls without losing sensitivity. An adjustment step (such as a maximization step in an EM algorithm) can be set up by assuming that the capture probe follows a Bernoulli distribution with a probability of being spurious. The probability of a capture probe i for test sequencing library j being spurious given the prior $\pi_j$ can be written as:

$$p(b_i|\pi_j)=\pi_j^{b_i}(1-\pi_j)^{1-b_i}$$

As the Bernoulli distribution limits $b_i$ to be either 0 or 1, the above probability is set to $\pi_j$ (when $b_i$=1), or $1-\pi_i$ (when $b_i$=0).

Given the determined number of sequencing reads mapped to spatially adjacent segments (or spatially adjacent sub-segments) 0 to I, the probability of capture probe i being spurious can be derived to:

$$p(b_i \mid k_{[0,1]}) = \frac{1}{1 + \sum_{x\in[0,C]} NegBinom(k_i \mid c_i)}$$

Given the expectation of the indicator $b_i$, the test sequencing library prior $\pi_j$ can be determined as:

$$\pi_j=\Pi\langle b_i\rangle_{k[0,I]}-1$$

In some embodiments, the most probable copy number of the interrogated segment or the one or more sub-segments of the interrogated segment is not called if the capture probe associated with the interrogated segment is determined to be spurious. In some embodiments, the most probable copy number of the interrogated segment or the one or more sub-segments of the interrogated segment is not called if the probability of a capture probe i being spurious (that is, $p(b_i|k_{[0,1]})$) is above a predetermined threshold (such as about 0.1 or more, about 0.2 or more, about 0.3 or more, about 0.4 or more, or about 0.5 or more).

In some embodiments, there is a method for determining a copy number of an interrogated segment or a sub-segment of the interrogated segment within a region of interest comprising: (a) mapping a plurality of sequencing reads generated from a test sequencing library to the interrogated segment, wherein the test sequencing library is enriched using one or more capture probes; (b) determining a number of sequencing reads mapped to the interrogated segment; (c) determining a copy number likelihood model based on an expected number of sequencing reads mapped to the interrogated segment; (d) building a hidden Markov model comprising: (i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model; (e) parameterizing the hidden Markov model by adjusting the copy number likelihood model to fit the determined number of sequencing reads mapped to the interrogated segment and accounting for one or more spurious capture probes; and (f) determining a most probable copy number of the interrogated segment or a sub-segment of the interrogated segment based on the parameterized hidden Markov model.

In some embodiments, there is a method for determining a copy number of an interrogated segment or a sub-segment of the interrogated segment within a region of interest comprising: (a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent direct targeted sequencing capture probes; (b) determining a number of sequencing reads mapped to each spatially adjacent segment; (c) determining a copy number likelihood model for each spatially adjacent segment based on an expected number of mapped sequencing reads at the spatially adjacent segment; (d) building a hidden Markov model comprising: (i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; (e) parameterizing the hidden Markov model comprising adjusting each copy number likelihood model to fit the determined number of sequencing reads mapped to each spatially adjacent segment and accounting for one or more spurious capture probes; and (f) determining a most probable copy number of the interrogated segment or a sub-segment of the interrogated segment based on the parameterized hidden Markov model.

Noisy Test Sequencing Library

Figure 6A:
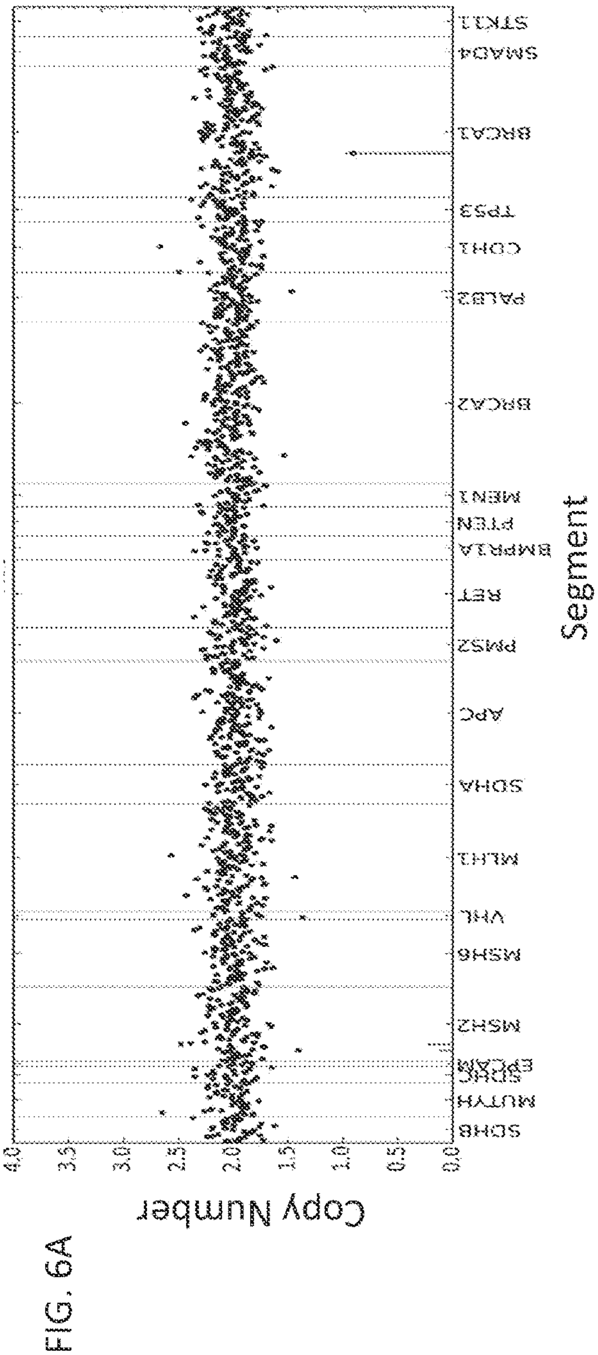
FIG. 6A shows the determined copy number for a plurality of segments across 22 genes for a less noisy test sequencing library.
Figure 6B:
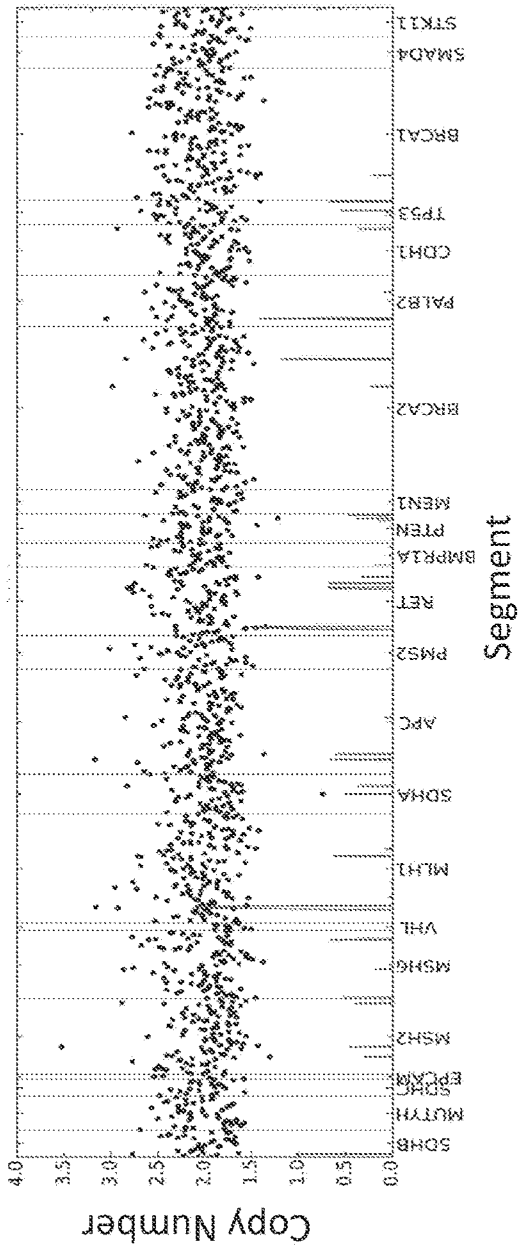
FIG. 6B shows the determined copy number for a plurality of segments across 22 genes for a noisier test sequencing library. The two different test sequencing libraries were enriched with the same capture probes display different levels of noise.

During preparation of test sequencing libraries, several steps can result in the nucleic acid of the test sequencing library to be more prone to "noise" across multiple capture probes. This results in inconsistent data and a high number of false positives FIG. 6A shows an example of a less noisy test sequencing library and FIG. 6B shows an example of a noisier test sequencing library, even though the two sequencing libraries were enriched using the same capture probe library. Noise can be introduced, for example, during preparation or sequencing of the test sequencing library, isolation of the nucleic acids from a test sample, storage of the sequencing library, or fragmentation of the nucleic acids isolated from the test sample can compromise the integrity of the oligonucleotide, which in turn can affect how the oligonucleotide.

In some embodiments, parameterizing the hidden Markov model comprises accounting for noise in the number of mapped sequencing reads. In some embodiments, accounting for noise in the number of mapped sequencing reads comprises adjusting the copy number likelihood model. For example, parameterizing the hidden Markov model can include an expectation-maximization step, and accounting for the noise can occur during the expectation-maximization step.

The dispersion d of the copy number likelihood distribution in the copy number likelihood model was discussed above. When only the dispersion due to the capture probe (i.e., at the segment) is considered, $d=d_i$. The dispersion of the copy number likelihood distribution can also be used to account for noise across the segments in the test sequencing library j. Thus, the dispersion of the copy number likelihood distribution can formally be considered as:

$$d=d_i*d_j$$

Parameterization of the hidden Markov model adjusts the copy number likelihood model, including the dispersion of the copy number likelihood distributions with the model. Thus, both components of the dispersion d (that is, $d_i$ and $d_j$) can be adjusted during parameterization of the hidden Markov model, for example using an expectation maximization algorithm. In some embodiments, a quasi-Newton method can be used to account for the noise during the maximization step. In particular, the expectation step asks to maximize the following $$\left\langle l\left(\vec{\mu},\vec{d}\right)\right\rangle_{k[0,T]} = \sum_{\substack{i\in TSLs \\ j\in cpt\ probes}} p(x_{ij}=2\,|\,k[0,T])\,p(b_{ij}=0\,|\,k[0,T])\ln NegBinom\left(k_{ij}\,|\,x_{i,j},\vec{\mu},\vec{d}\right)$$

In the equation, $l(\vec{\mu}, \vec{d})$ represents the expected logarithmic likelihood given all the data and the current parameters of the model. TSL stands for test sequencing library and cpt probes refers to capture probes. The mean $\vec{\mu}$ can be approximated by using a double normalization, which accounts for both the median sequencing depth across segments within a test sequencing library and the median sequencing depth of a plurality of test sequencing library across the same segment. In some embodiments, to find the dispersion $\vec{d}$ that can maximize this function a quasi- Newtonian method is used. The quasi-Newton method sets the partial derivative of this function with respect to $\vec{d}$ to 0. Since the test sequencing library and the capture probe shape are independent, it is equivalent to setting the partial derivative of each type to 0.

$$\frac{\partial\langle l(\vec{\mu},\vec{d})\rangle_{k[0,T]}}{\partial\vec{d}} = \frac{\partial\langle l(\vec{\mu},\vec{d})\rangle_{k[0,T]}}{\partial d_i}, \frac{\partial\langle l(\vec{\mu},\vec{d})\rangle_{k[0,T]}}{\partial d_j}$$

Once the parameters of the distribution are set, the parameterized hidden Markov model can be used to determine the most probable copy number state of the segment.

Computer Systems

Further contemplated herein are computing system configured to perform any one of the processes described herein, including the various exemplary processes for determining a copy number of an interrogated segment or determining a copy number variant abnormality within a region of interest. In this context, the computing system may include, for example, a processor, memory, storage, and input/output devices (e.g., monitor, keyboard, disk drive, Internet connection, etc.). However, the computing system may include circuitry or other specialized hardware for carrying out some or all aspects of the processes. In some operational settings, the computing system may be configured as a system that includes one or more units, each of which is configured to carry out some aspects of the processes either in software, hardware, or some combination thereof.

In some embodiments the computing system includes a number of components that may be used to perform the processes described herein. The system can include a motherboard having an input/output ("I/O") section, one or more central processing units ("CPU"), and a memory section, which may have a flash memory card related to it. The I/O section can be connected to a display, a keyboard, a disk storage unit, and a media drive unit. The media drive unit can read/write a computer-readable medium, which can contain programs (i.e., instructions) and/or data.

At least some values based on the results of the processes described herein can be saved for subsequent use. Additionally, a non-transitory computer-readable medium can be used to store (e.g., tangibly embody) one or more computer programs for performing any one of the above-described processes by means of a computer. The computer program may be written, for example, in a general-purpose programming language (e.g., Pascal, C, C++, Java, Python, JSON, etc.) or some specialized application-specific language.

EXEMPLARY EMBODIMENTS

Embodiment 1. A method for determining a copy number of an interrogated segment within a region of interest comprising:

(a) mapping a plurality of sequencing reads generated from a test sequencing library to the interrogated segment, wherein the test sequencing library is enriched using one or more direct targeted sequencing capture probes;

(b) determining a number of sequencing reads mapped to the interrogated segment;

(c) determining a copy number likelihood model based on an expected number of sequencing reads mapped to the interrogated segment;

(d) building a hidden Markov model comprising:

(i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model;

(e) parameterizing the hidden Markov model by adjusting the copy number likelihood model to fit the determined number of sequencing reads mapped to the interrogated segment; and (f) determining a most probable copy number of the interrogated segment based on the parameterized hidden Markov model.

Embodiment 2. A method for determining a copy number of an interrogated segment within a region of interest comprising:

(a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent direct targeted sequencing capture probes;

(b) determining a number of sequencing reads mapped to each spatially adjacent segment;

(c) determining a copy number likelihood model for each spatially adjacent segment based on an expected number of mapped sequencing reads at the spatially adjacent segment;

(d) building a hidden Markov model comprising:

(i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment;

(e) parameterizing the hidden Markov model comprising adjusting each copy number likelihood model to fit the determined number of sequencing reads mapped to each spatially adjacent segment; and (f) determining a most probable copy number of the interrogated segment based on the parameterized hidden Markov model.

Embodiment 3. The method of embodiment 1 or 2, further comprising determining a most probable copy number of a section within the region of interest, wherein the section comprises a plurality of spatially adjacent segments comprising the interrogated segment.

Embodiment 4. The method of any one of embodiments 1-3, wherein the copy number likelihood model comprises a distribution for two or more copy number states.

Embodiment 5. The method of any one of embodiments 1-4, wherein the copy number likelihood model comprises a negative binomial distribution, wherein the negative binomial distribution is not a Poisson distribution.

Embodiment 6. The method of any one of embodiments 1-5, wherein the expected number of sequencing reads is based on an average number of mapped sequencing reads at a corresponding segment across a plurality of sequencing libraries and an average number of mapped sequencing reads across a plurality of segments of interest within the test sequencing library, wherein the average number of mapped sequencing reads at a corresponding segment across a plurality of sequencing libraries or the average number of mapped sequencing reads across a plurality of segments of interest within the test sequencing library is a normalized average.

Embodiment 7. The method of any one of embodiments 1-6, wherein the copy number likelihood model is adjusted to account for the presence of GC content bias.

Embodiment 8. The method of embodiment 6 or 7, wherein the adjustment depends on the GC content of the capture probe corresponding to the interrogated segment or the GC content of the interrogated segment.

Embodiment 9. The method of any one of embodiments 1-8, wherein the hidden Markov model comprises a transition probability of the copy number of the interrogated segment for a given copy number of a spatially adjacent segment.

Embodiment 10. The method of any one of embodiments 1-9, wherein the hidden Markov model comprises a plurality of transition probabilities of the copy number of a sub-segment in the plurality of sub-segments within the interrogated segment for a given copy number of a spatially adjacent sub-segment.

Embodiment 11. The method of embodiment 9 or 10, wherein the transition probability accounts for an average length of a copy number variant.

Embodiment 12. The method of any one of embodiments 9-11, wherein the transition probability accounts for a prior probability of a copy number variant at the interrogated segment or a spatially adjacent segment.

Embodiment 13. The method of embodiment 11 or 12, wherein the average length of a copy number variant or the probability of a copy number variant at the interrogated segment are determined based on observations in a human population.

Embodiment 14. The method of any one of embodiments 1-13, wherein parameterizing the hidden Markov model comprises accounting for one or more spurious capture probes.

Embodiment 15. The method of embodiment 14, wherein accounting for one or more spurious capture probes comprises weighting the one or more observation states in the plurality of observation states with a spurious capture probe indicator.

Embodiment 16. The method of embodiment 15, wherein the spurious capture probe indicator is determined using a Bernoulli process.

Embodiment 17. The method of embodiment 15 or 16, wherein accounting for one or more of the capture probes being spurious comprises using expectation-maximization.

Embodiment 18. The method of any one of embodiments 14-17, wherein if a capture probe is determined to be spurious, the likelihood information from that capture probe is disregarded in the copy number likelihood model.

Embodiment 19. The method of any one of embodiments 1-18, wherein the parameterizing of the hidden Markov model comprises accounting for noise in the number of mapped sequencing reads.

Embodiment 20. The method of any one of embodiments 1-19, wherein accounting for noise in the number of mapped sequencing reads comprises adjusting the copy number likelihood model.

Embodiment 21. The method of embodiment 20, wherein adjusting the copy number likelihood model to account for the noise comprises an expectation-maximization step.

Embodiment 22. The method of embodiment 21 wherein the expectation-maximization step comprises weighing a level of noise in the number of mapped sequencing reads from the test sequencing library.

Embodiment 23. The method of embodiment 22, wherein the expectation-maximization step comprises using a Quasi-Newtonian solver.

Embodiment 24. The method of any one of embodiments 19-23, wherein the most probable copy number of the interrogated segment is not called if the noise in the number of mapped sequencing reads is above a predetermined threshold.

Embodiment 25. The method of any one of embodiments 1-24, wherein sequencing reads from overlapping capture probes are merged.

Embodiment 26. The method of any one of embodiments 1-25, wherein a Viterbi algorithm, a Quasi-Newton solver, or a Markov chain Monte Carlo is used to determine the most probable copy number of the interrogated segment.

Embodiment 27. The method of any one of embodiments 1-26, further comprising determining a confidence of the most probable copy number of the segment.

Embodiment 28. The method of any one of embodiments 1-27, wherein the region of interest is a region within genomic DNA.

Embodiment 29. The method of any one of embodiments 1-28, wherein the test sequencing library is derived from cell-free DNA.

Embodiment 30. The method of any one of embodiments 1-29, further comprising reporting the most probable copy number of the interrogated segment.

Embodiment 31. The method of any one of embodiments 1-29, further comprising reporting a copy number variant.

Embodiment 32. The method of embodiment 31, wherein the copy number variant is reported to a patient or a healthcare provider.

Embodiment 33. The method of any one of embodiments 1-32, further comprising providing a medical diagnosis based on the most probable copy number of the interrogated segment.

Embodiment 34. The method of any one of embodiments 1-33, further comprising suggesting a treatment regimen based on the most probable copy number of the interrogated segment.

Embodiment 35. A method for determining a copy number variant abnormality within a region of interest, comprising:

(a) mapping a plurality of sequencing reads generated from a test sequencing library to an interrogated segment within the region of interest, wherein the test sequencing library is enriched using one or more direct targeted sequencing capture probes;

(b) determining a number of sequencing reads mapped to the interrogated segment;

(c) determining a copy number likelihood model based on an expected number of sequencing reads mapped to the interrogated segment;

(d) building a hidden Markov model comprising:
(i) one or more hidden states comprising a copy number corresponding to the interrogated segment or a plurality of sub-segments within the interrogated segment,
(ii) an observation state comprising the number of sequencing reads mapped to the interrogated segment; and
(iii) the copy number likelihood model;
(e) parameterizing the hidden Markov model by adjusting the copy number likelihood model to fit the determined number of sequencing reads mapped to the interrogated segment; and
(f) determining a most probable copy number of the interrogated segment based on the parameterized hidden Markov model;
(g) determining a copy number variant abnormality based on the most probable copy number of the interrogated segment.

Embodiment 36. A method for determining a copy number variant abnormality within a region of interest, comprising:
(a) mapping a plurality of sequencing reads generated from a test sequencing library to a plurality of spatially adjacent segments, wherein the plurality of spatially adjacent segments comprises an interrogated segment, and wherein the test sequencing library is enriched using a plurality of spatially adjacent direct targeted sequencing capture probes;
(b) determining a number of sequencing reads mapped to each spatially adjacent segment;
(c) determining a copy number likelihood model for each spatially adjacent segment based on an expected number of mapped sequencing reads at the spatially adjacent segment;
(d) building a hidden Markov model comprising:
(i) a plurality of hidden states comprising a copy number for each of the spatially adjacent segments or a plurality of sub-segments within each of the spatially adjacent segments,
(ii) a plurality of observation states comprising the number of sequencing reads mapped to each spatially adjacent segment, and
(iii) the copy number likelihood model for each spatially adjacent segment;
(e) parameterizing the hidden Markov model comprising adjusting each copy number likelihood model to fit the determined number of sequencing reads mapped to each spatially adjacent segment; and
(f) determining a most probable copy number of the interrogated segment based on the parameterized hidden Markov model;
(g) determining a copy number variant abnormality based on the most probable copy number of the interrogated segment.

Embodiment 37. A method for determining a copy number of an interrogated segment within a region of interest comprising:
(a) mapping a plurality of sequencing reads generated from a test sequencing library to a plurality of segments within a region of interest, wherein the test sequencing library is enriched using a plurality of capture probes, and wherein the plurality of segments comprises the interrogated segment;
(b) determining a number of sequencing reads mapped to each segment;
(c) determining a copy number likelihood model for the segment based on an expected number of mapped sequencing reads at each segment, wherein the expected number of mapped sequencing reads is corrected for GC content of the segment; and
(d) determining a most probable copy number of the interrogated segment based on the copy number likelihood model.

Embodiment 38. A method for determining a copy number of an interrogated segment within a region of interest comprising:
(a) mapping a plurality of sequencing reads generated from a test sequencing library to the interrogated segment, wherein the test sequencing library is enriched using a plurality of capture probes;
(b) determining a number of sequencing reads mapped to the interrogated segment;
(c) determining a copy number likelihood model based on an expected number of sequencing reads mapped to the interrogated segment, wherein the expected number of mapped sequencing reads is corrected for GC content of the interrogated segment;
(d) building a hidden Markov model comprising:
(i) one or more hidden states comprising a copy number corresponding to the interrogated segment or a plurality of sub-segments within the interrogated segment,
(ii) an observation state comprising the number of sequencing reads mapped to the interrogated segment; and
(iii) the copy number likelihood model;
(e) parameterizing the hidden Markov model by adjusting the copy number likelihood model to fit the determined number of sequencing reads mapped to the interrogated segment; and
(f) determining a most probable copy number of the interrogated segment based on the parameterized hidden Markov model.

Embodiment 39. A method for determining a copy number of an interrogated segment within a region of interest comprising:
(a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent capture probes;
(b) determining a number of sequencing reads mapped to each spatially adjacent segment;
(c) determining a copy number likelihood model for each spatially adjacent segment based on an expected number of mapped sequencing reads at the spatially adjacent segment, wherein the expected number of mapped sequencing reads is corrected for GC content of the spatially adjacent segment;
(d) building a hidden Markov model comprising:
(i) a plurality of hidden states comprising a copy number for each of the spatially adjacent segments or a plurality of sub-segments within each of the spatially adjacent segments,
(ii) a plurality of observation states comprising the number of sequencing reads mapped to each spatially adjacent segment, and
(iii) the copy number likelihood model for each spatially adjacent segment;
(e) parameterizing the hidden Markov model comprising adjusting each copy number likelihood model to fit the determined number of sequencing reads mapped to each spatially adjacent segment; and (f) determining a most probable copy number of the interrogated segment based on the parameterized hidden Markov model.

Embodiment 40. The method of any one of embodiments 37-39, wherein the capture probes are direct targeted sequencing capture probes.

Embodiment 41. The method of any one of embodiments 37-40, wherein the capture probes enrich the sequencing library using hybrid capture techniques.

Embodiment 42. The method of any one of embodiments 37-41, wherein the expected number of sequencing reads is corrected for the GC content by multiplying the expected number of sequencing reads at any given segment by a GC bias correction factor for that segment, wherein the GC bias correction factor is determined for the test sequencing library.

Embodiment 43. The method of embodiment 42, wherein the GC bias correction factor is determined by:

fitting a second order function to a plurality of data points, wherein the data points each comprises a normalized number of sequencing reads mapped to a segment and the GC content of that segment, and wherein the plurality of data points represent a plurality of segments enriched by the capture probes in the test sequencing library; and defining the GC bias correction factor to be the normalized number of sequencing reads determined by the second order function for the GC content of the segment.

Embodiment 44. A method for determining a copy number of an interrogated segment within a region of interest comprising:

(a) mapping a plurality of sequencing reads generated from a test sequencing library to the interrogated segment, wherein the test sequencing library is enriched using one or more capture probes;

(b) determining a number of sequencing reads mapped to the interrogated segment;

(c) determining a copy number likelihood model based on an expected number of sequencing reads mapped to the interrogated segment;

(d) building a hidden Markov model comprising:

(i) one or more hidden states comprising a copy number corresponding to the interrogated segment or a plurality of sub-segments within the interrogated segment, (ii) an observation state comprising the number of sequencing reads mapped to the interrogated segment; and (iii) the copy number likelihood model;

(e) parameterizing the hidden Markov model by adjusting the copy number likelihood model to fit the determined number of sequencing reads mapped to the interrogated segment and accounting for one or more spurious capture probes; and (f) determining a most probable copy number of the interrogated segment based on the parameterized hidden Markov model.

Embodiment 45. A method for determining a copy number of an interrogated segment within a region of interest comprising:

(a) mapping a plurality of sequencing reads generated from a test sequencing library to a plurality of spatially adjacent segments, wherein the plurality of spatially adjacent segments comprises the interrogated segment, and wherein the test sequencing library is enriched using a plurality of spatially adjacent direct targeted sequencing capture probes;

(b) determining a number of sequencing reads mapped to each spatially adjacent segment;

(c) determining a copy number likelihood model for each spatially adjacent segment based on an expected number of mapped sequencing reads at the spatially adjacent segment;

(d) building a hidden Markov model comprising:

(i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment;

(e) parameterizing the hidden Markov model comprising adjusting each copy number likelihood model to fit the determined number of sequencing reads mapped to each spatially adjacent segment and accounting for one or more spurious capture probes; and (f) determining a most probable copy number of the interrogated segment based on the parameterized hidden Markov model.

Embodiment 46. The method of embodiment 44 or 45, wherein accounting for one or more spurious capture probes comprises weighting the one or more observation states in the plurality of observation states with a spurious capture probe indicator.

Embodiment 47. The method of embodiment 46, wherein the spurious capture probe indicator is determined using a Bernoulli process.

Embodiment 48. The method of embodiment 46 or 47, wherein accounting for one or more of the capture probes being spurious comprises using expectation-maximization.

Embodiment 49. The method of any one of embodiments 44-48, wherein the most probable copy number of the interrogated segment or the one or more sub-segments of the interrogated segment is not called if the capture probe associated with the interrogated segment is determined to be spurious.

Embodiment 50. The method of any one of embodiments 44-48, wherein the most probable copy number of the interrogated segment or the one or more sub-segments of the interrogated segment is not called if the probability of a capture probe being spurious is above a predetermined threshold.

Embodiment 51. The method of any one of embodiments 44-50, wherein the capture probes are direct targeted sequencing capture probes.

Embodiment 52. The method of any one of embodiments 44-50, wherein the capture probes enrich the sequencing library using hybrid capture techniques.

Embodiment 53. The method of any one of embodiments 1-52, wherein the interrogated segment is at least 100 bases in length.

Embodiment 54. A computer system comprising a computer-readable medium comprising instructions for carrying out the method of any one of embodiments 1-53.

Example

The following example illustrates using a hidden Markov model to call the copy number state for segments within the BRCA1 and BRCA2 genes. Approximately 450 capture probes were used to enrich the BRCA gene from 48 different sequencing libraries by direct targeted sequencing. Each capture probe corresponds to a segment within the gene. The first nucleotide of each segment of interest corresponds to the first nucleotide of the sequence that hybridizes to the capture probe mapped at the segment of interest. Enriched sequencing libraries were then sequenced using an Illumina HiSeq 2500 next generation sequencer.

Sequencing of the 48 test sequencing libraries generated multiple sequencing reads. Sequencing reads were mapped to the segments within the BRCA gene. Overlapping and correlated capture probes were merged to correspond to a single segment. Once it is accounted for merging or overlapping probes, a number of mapped sequencing reads was determined for each segment within the region of interest.

The number of mapped sequencing reads was used to determine the most probable copy number state for each of the segments. First a copy number likelihood model was built comprising a negative binomial distribution (wherein the negative binomial distribution is not a Poisson distribution) for the expected number of sequencing reads for a copy number state of 0, 1, 2, 3 and 4 for each of the segments for each of the 48 test sequencing libraries. The copy number likelihood distributions in the model gave a probability that that the copy number for that distribution was correct given the observed number of sequencing reads. The most probable copy number state for the majority the segments in each of the test sequencing libraries was 2.

Each segment was divided into sub-segments of 1 nucleotide each. A hidden Markov model was built with a hidden state (a hidden copy number) for each sub-segment, an observation state (the determined number of mapped sequencing reads) for each segment, and the copy number likelihood model to indicate the probability of the observed state given the hidden state. The hidden Markov model also included transition probabilities between spatially adjacent segments (that is, between the hidden states). The following stochastic transition matrix was used to represent the transition probability of a copy number state of a subsequent spatially adjacent sub-segment given the copy number state of a preceding spatially adjacent sub-segment.

$$p(C_{i+1} \mid C_i) = \begin{bmatrix} 1 - r_{01} & r_{10} & 0 & 0 & 0 \\ r_{01} & 1 - r_{12} - r_{10} & r_{21} & 0 & 0 \\ 0 & r_{12} & 1 - r_{23} - r_{21} & r_{32} & 0 \\ 0 & 0 & r_{23} & 1 - r_{32} - r_{34} & r_{43} \\ 0 & 0 & 0 & r_{34} & 1 - r_{43} \end{bmatrix}$$

wherein $C_i$ is the copy number state of a first sub-segment; $C_{i+1}$ is the copy number state of the second sub-segment; and $r_{ab}$ represents transition from a copy state of a to a copy state of b. To set the transition, the average length of a copy number variant in human populations and the probability of observing a copy number variant in human populations were taken into account. Specifically the transitions were set based on the following formulas:

$$r_{01} = r_{12} = r_{32} = r_{43} = \frac{1}{\langle l \rangle_{CNV}}$$

$$r_{21} = r_{12} \frac{p_{CNV}}{1 - 2p_{CNV} - 2p_{CNV}^2}$$

wherein $\langle l \rangle_{CNV}$ denotes the length of a copy number variant and was set to 6200 nucleotides; and wherein $P_{CNV}$ denotes the probability of a copy number variant which was set to 0.001. The probability of the copy number variant was set by balancing the thresholds for confident calling and retesting of calls to achieve the desired sensitivity and specificity, but the prior is set irrespective of the validation. Subsequently the threshold can be tuned based on the frequency of a copy number call within the region.

The hidden Markov model was parameterized to adjust the copy number likelihood model (which accounted for GC content bias), as well as to account for spurious capture probes and noise within the test sequencing libraries. Optimization was done using Expectation-Maximization algorithms. The Baum-Welch was used for the Expectation step and the Quasi-Newton was used for the Maximization step. A Viterbi algorithm was used to determine the most probable copy number at each segment.

Figure 7:
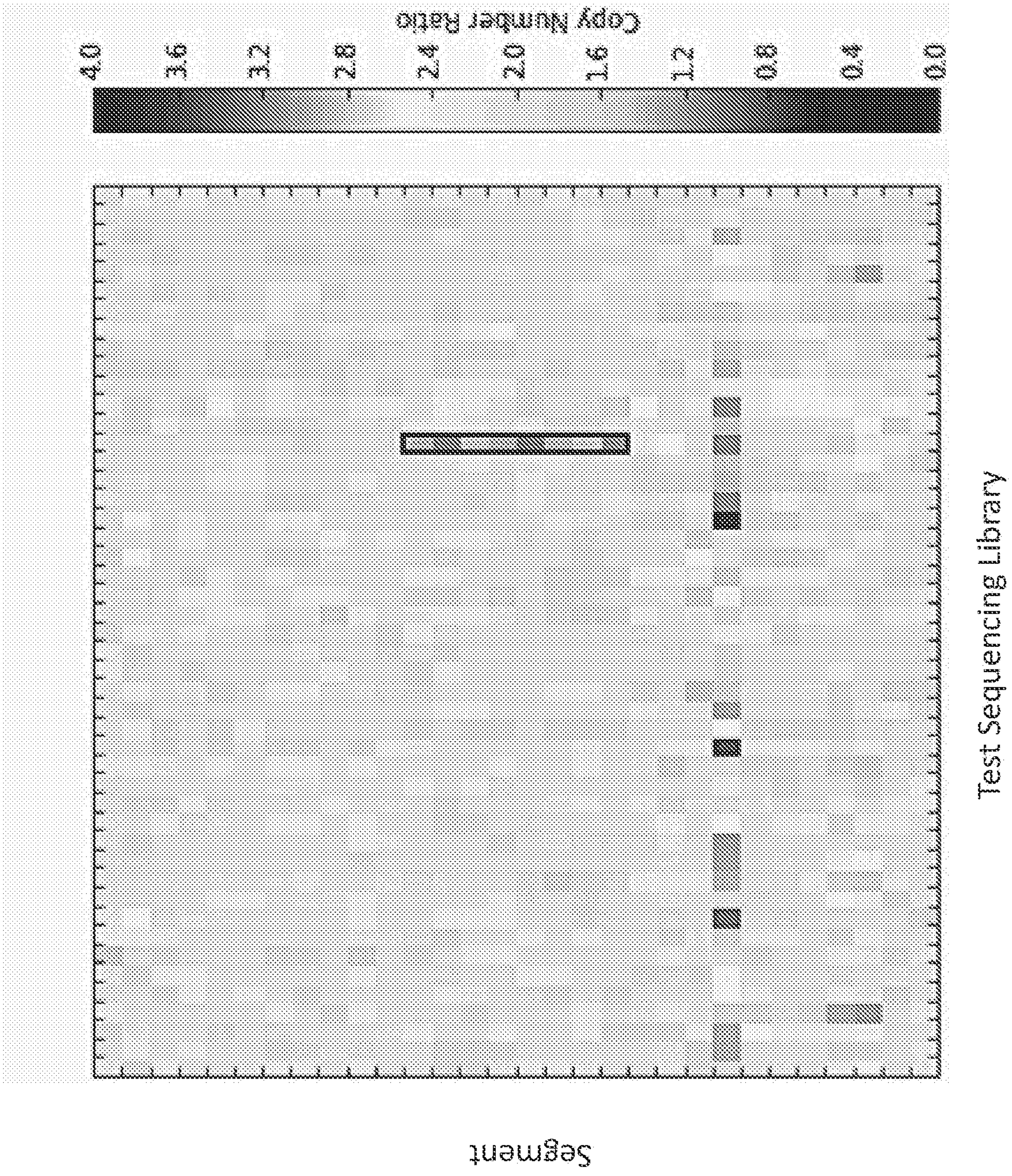
FIG. 7 shows copy number calls across multiple segments within the same region of interest (y-axis) for several test sequencing libraries (x-axis) relying only on a copy number likelihood model. Darker shaded areas show a deviation from a copy number state of two. The boxed region shows how a true copy number variant spans across multiple segments, whereas deviations from a copy number state of two which are only observed within a segment are likely to be false positives rather than true copy number variants.
Figure 8:
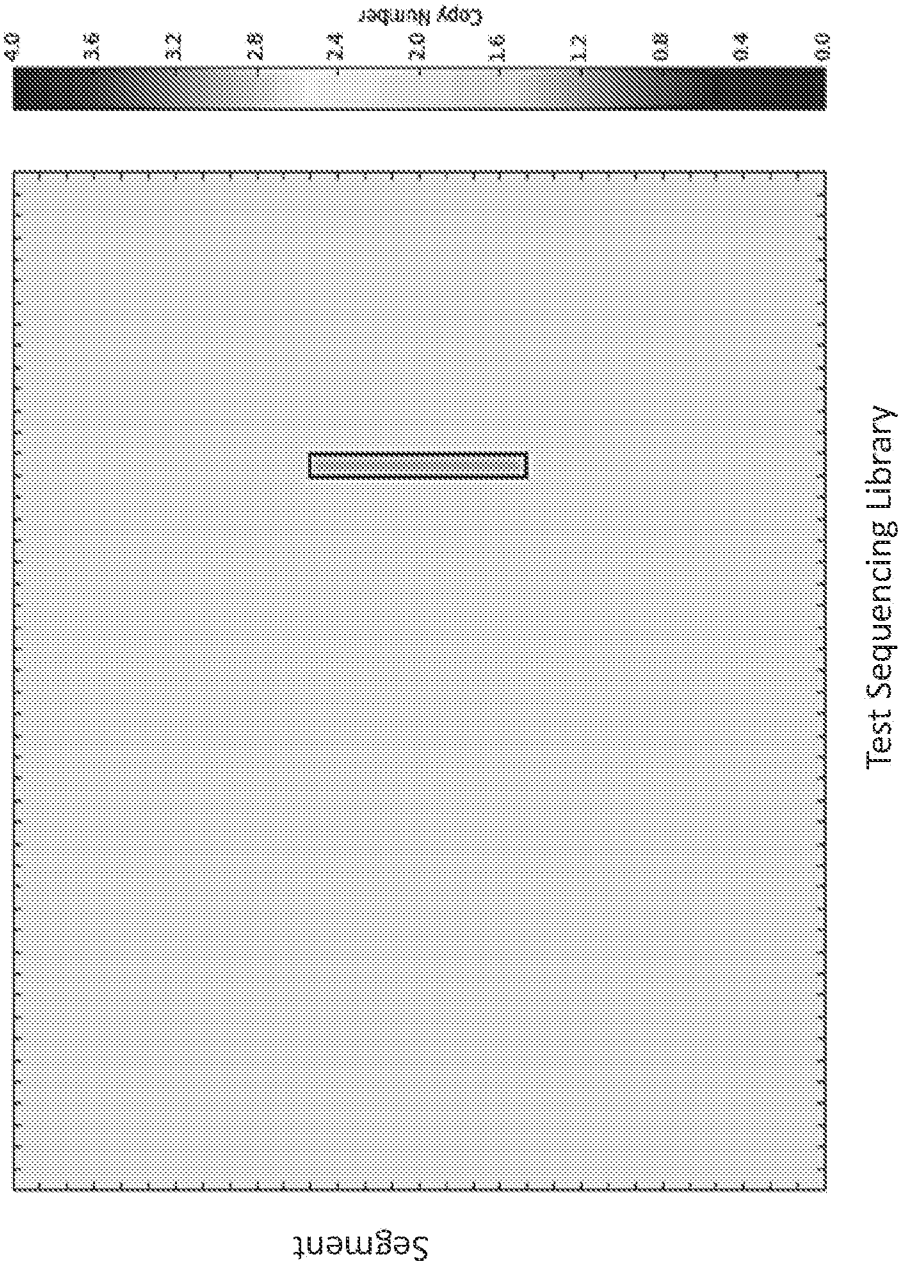
FIG. 8 shows copy number calls across multiple segments within the same region of interest (y-axis) for several test sequencing libraries (x-axis) after the determining the most probably copy number using a hidden Markov model. Darker shaded areas show a deviation from a copy number state of two. The boxed region shows how a true copy number variant spans across multiple segments, and false positives are minimized. The HMM takes into consideration the effect that a copy number state of an adjacent segment has on subsequent segments. This allows the model to call true copy number variants, as opposed to variations that are observed within a single segment.

While the copy number (i.e., the hidden state) was determined for each nucleotide within the BRCA gene, the most likely copy number call was made for each segment. This allows the model to discriminate and discard very small insertion or deletion that would not constitute a copy number variant. FIG. 7 shows the copy number state for a portion of the spatially adjacent segments within the BRCA gene across all test sequencing libraries without using the parameterized hidden Markov model (that is, using the copy number likelihood model alone). FIG. 8 shows the most likely copy number after parameterizing the hidden Markov model and determining a most probable copy number of the segments based on the parameterized hidden Markov model.

What is claimed is:

1. A system for determining a copy number of an interrogated segment of nucleic acids within a region of interest of a genome, the system comprising a non-transitory computer-readable storage medium programed to:

(a) obtain a plurality of sequencing reads from a test sequencing library (b) map the plurality of sequencing reads with the interrogated segment; and (c) determine the copy number of the interrogated segment, wherein the copy number is the most probable copy number of the interrogated segment as determined by an optimized parameterized hidden Markov model comprising:

(i) one or more hidden states comprising a copy number corresponding to the interrogated segment or a plurality of sub-segments within the interrogated segment;

(ii) an observation state comprising a number of sequencing reads mapped to the interrogated segment; and (iii) a copy number likelihood model using one or more likelihood distributions for an expected number of sequencing reads mapped to the interrogated segment, wherein the hidden Markov model is parameterized by adjusting the copy number likelihood model to fit the determined number of sequencing reads mapped to the interrogated segment by allowing portions of the likelihood distributions to float.

2. The system of claim 1, wherein the system is further operable to:

map the plurality of sequencing reads to a plurality of spatially adjacent segments, wherein the plurality of spatially adjacent segments comprises the interrogated segment;

determine a copy number likelihood model for each spatially adjacent segment using a plurality of likelihood distributions associated with an expected number of mapped sequencing reads at the spatially adjacent segment;

build the hidden Markov model, wherein the hidden Markov model comprises comprising:

(i) a plurality of hidden states comprising a copy number for each of the spatially adjacent segments or a plurality of sub-segments within each of the spatially adjacent segments, (ii) a plurality of observation states comprising the number of sequencing reads mapped to each spatially adjacent segment, and (iii) the copy number likelihood model for each spatially adjacent segment; and parameterizing the hidden Markov model comprising adjusting each copy number likelihood model to fit the determined number of sequencing reads mapped to each spatially adjacent segment by allowing portions of the likelihood distributions to float.

3. The system of claim 1, wherein the system is further operable to determine a most probable copy number of a section within the region of interest, wherein the section comprises a plurality of spatially adjacent segments comprising the interrogated segment.

4. The system of claim 1, wherein the copy number likelihood model comprises a distribution for two or more copy number states or a negative binomial distribution, wherein the negative binomial distribution is not a Poisson distribution.

5. The system of claim 1, wherein the expected number of sequencing reads is based on an average number of mapped sequencing reads at a corresponding segment across a plurality of sequencing libraries and an average number of mapped sequencing reads across a plurality of segments of interest within the test sequencing library, wherein the average number of mapped sequencing reads at a corresponding segment across a plurality of sequencing libraries or the average number of sequencing reads across a plurality of segments of interest within the test sequencing library is a normalized average.

6. The system of claim 1, wherein the copy number likelihood model is adjusted to account for the presence of GC content bias, and wherein adjustment of the copy number likelihood model depends on the GC content of the capture probe corresponding to the interrogated segment or the GC content of the interrogated segment.

7. The system of claim 1, wherein the hidden Markov model comprises a plurality of transition probabilities of the copy number of a sub-segment in the plurality of sub-segments within the interrogated segment for a given copy number of a spatially adjacent sub-segment.

8. The system of claim 1, wherein the hidden Markov model comprises a transition probability of the copy number of the interrogated segment for a given copy number of a spatially adjacent segment, wherein the transition probability accounts for an average length of a copy number variant or for a prior probability of a copy number variant at the interrogated segment or a spatially adjacent segment, wherein the average length of a copy number variant or the probability of a copy number variant at the interrogated segment are determined based on observations in a human population.

9. The system of claim 1, wherein the system is further operable to parameterize the hidden Markov model by accounting for one or more spurious capture probes, wherein accounting for one or more spurious capture probes comprises weighting the one or more observation states in the plurality of observation states with a spurious capture probe indicator or optimizing the parameterized hidden Markov model using an expectation-maximization step, wherein the spurious capture probe indicator comprises a Bernoulli distribution of a prior observation state in the hidden Markov model, and if a capture probe is determined to be spurious, the likelihood information from that capture probe is disregarded in the copy number likelihood model.

10. The system of claim 1, wherein the system is further operable to parameterize the hidden Markov model by accounting for noise in the number of mapped sequencing reads, wherein accounting for noise in the number of mapped sequencing reads comprises adjusting the copy number likelihood model by adjusting a dispersion of a copy number likelihood distribution in the copy number likelihood model, wherein adjusting the copy number likelihood model to account for the noise comprises adjusting the dispersion of the copy number likelihood distribution in the copy number likelihood model via an expectation-maximization step, wherein the expectation-maximization step comprises weighing a level of noise in the number of mapped sequencing reads from the test sequencing library, wherein the expectation-maximization step comprises using a Quasi-Newtonian solver, and wherein the most probable copy number of the interrogated segment is not called if the noise in the number of mapped sequencing reads is above a predetermined threshold.

11. The system of claim 1, wherein sequencing reads from overlapping capture probes are merged.

12. The system of claim 1, wherein the system is further operable to implement a Viterbi algorithm to determine the most probable copy number of the interrogated segment.

13. The system of claim 1, wherein the system is further operable to determine a confidence of the most probable copy number of the segment.

* * * * *